US012648829B2

(12) United States Patent
Hastings et al.

(10) Patent No.: US 12,648,829 B2
(45) Date of Patent: Jun. 9, 2026

(54) SYSTEMS AND METHODS FOR DISPLAYING INTRAOPERATIVE IMAGE DATA

(71) Applicant: Stryker Corporation, Kalamazoo, MI (US)

(72) Inventors: Sean Victor Hastings, Flower Mound, TX (US); Heather Michelle Bartlett, Dallas, TX (US); John Edward Musko, Irving, TX (US); Sudhanshu Mehta, Gurdaspur (IN); Avinash Kumar, Bokaro Steel City (IN); Robert Lee York, Lantana, TX (US)

(73) Assignee: Stryker Corporation, Portage, MI (US)

( * ) Notice: Subject to any disclaimer, the term of this patent is extended or adjusted under 35 U.S.C. 154(b) by 546 days.

(21) Appl. No.: 18/053,747

(22) Filed: Nov. 8, 2022

(65) Prior Publication Data

US 2023/0146466 A1 May 11, 2023

Related U.S. Application Data

(60) Provisional application No. 63/263,819, filed on Nov. 9, 2021.

(51) Int. Cl.
A61B 90/00 (2016.01)
A61B 34/20 (2016.01)

(52) U.S. Cl.
CPC ............ A61B 90/37 (2016.02); A61B 90/361 (2016.02); *A61B 2034/2065* (2016.02); *A61B 2090/371* (2016.02)

(58) Field of Classification Search
None
See application file for complete search history.

(56) References Cited

U.S. PATENT DOCUMENTS

| | | | |
|---|---|---|---|
| 7,224,472 B2 | 5/2007 | Bauch |
| 8,976,236 B2 | 3/2015 | Deland |
| 9,734,427 B2 | 8/2017 | Lin |
| | (Continued) | | |

FOREIGN PATENT DOCUMENTS

| | | | | |
|---|---|---|---|---|
| BR | 112020012974 A2 | * | 11/2020 | ......... A61B 1/00009 |
| CN | 105546405 A | | 5/2016 | |
| | (Continued) | | | |

OTHER PUBLICATIONS

English translation of BR-112020012974 (Year: 2020).*

(Continued)

*Primary Examiner* — Katherine L Fernandez

(74) *Attorney, Agent, or Firm* — Morrison & Foerster LLP

(57) ABSTRACT

An exemplary method of displaying an intraoperative image of a surgical site comprises: receiving a plurality of images captured by a plurality of in-light cameras integrated into one or more surgical light units illuminating the surgical site, wherein the plurality of images capture the surgical site from a plurality of different perspectives; identifying an obstruction to the surgical site in an image of the plurality of images; responsive to identifying the obstruction, generating a composite image based on a set of the plurality of images, wherein the composite image excludes the obstruction; and displaying the composite image as the intraoperative image of the surgical site.

26 Claims, 12 Drawing Sheets

(56) References Cited

U.S. PATENT DOCUMENTS

| | | | | |
|---|---|---|---|---|
| 9,886,746 | B2 | 2/2018 | Karande | |
| 10,303,185 | B2 | 5/2019 | Zhang | |
| 10,555,728 | B2 | 2/2020 | Charles | |
| 10,754,140 | B2 | 8/2020 | Chan | |
| 10,949,986 | B1 | 3/2021 | Colmenares | |
| 10,999,493 | B2 | 5/2021 | Coiseur | |
| 11,138,790 | B2 * | 10/2021 | Haslam | G06T 17/20 |
| 2006/0028489 | A1 | 2/2006 | Uyttendaele | |
| 2009/0086495 | A1 | 4/2009 | Chen | |
| 2013/0113909 | A1 * | 5/2013 | DeLand | A61B 50/28 |
| | | | | 348/77 |
| 2014/0005555 | A1 * | 1/2014 | Tesar | A61B 1/0004 |
| | | | | 600/476 |
| 2014/0268751 | A1 * | 9/2014 | Boccoleri | F21V 21/40 |
| | | | | 362/235 |
| 2016/0139039 | A1 | 5/2016 | Ikehara | |
| 2018/0330518 | A1 * | 11/2018 | Choi | G06N 3/045 |
| 2019/0045168 | A1 | 2/2019 | Chaudhuri | |
| 2019/0200848 | A1 | 7/2019 | Mcdowall | |
| 2019/0249847 | A1 * | 8/2019 | Hallack | A61B 90/30 |
| 2020/0014848 | A1 | 1/2020 | Gove | |
| 2020/0184248 | A1 * | 6/2020 | Donhowe | A61B 34/25 |
| 2020/0268471 | A1 * | 8/2020 | Kajita | H04N 7/18 |

FOREIGN PATENT DOCUMENTS

| | | | |
|---|---|---|---|
| CN | 107940300 | A | 4/2018 |
| CN | 109496257 | A | 3/2019 |
| CN | 111140792 | A | 5/2020 |
| CN | 111444752 | A | 7/2020 |
| CN | 112804515 | A | 5/2021 |
| KR | 10-2182649 | B1 | 11/2020 |
| WO | 2012/139218 | A1 | 10/2012 |
| WO | WO-2017042171 | A1 * | 3/2017 |
| WO | 2021/034681 | A1 | 2/2021 |

OTHER PUBLICATIONS

Extended European Search Report dated Apr. 3, 2023, directed to EP Application No. 22206416.4; 13 pages.

Hachiuma et al. (2020). "Deep Selection: A Fully Supervised Camera Selection Network for Surgery Recordings," Springer Nature Switzerland AG: 419-428.

Shimizu et al. "Automatic Viewpoint Switching for Multi-view Surgical Videos," 2019 IEEE International Symposium on Mixed and Augmented Reality Adjunct (ISMAR-Adjunct), Oct. 10-18, 2019, Beijing, China; 2 pages.

Shimizu et al. "Surgery Recording without Occlusions by Multi-view Surgical Videos," 15th International Joint Conference on Computer Vision, Imaging and Computer Graphics Theory and Applications, Feb. 27-29, 2020 Valletta, Malta; 8 pages.

Office Action dated Aug. 7, 2025, directed to EP Application No. 22 206 416.4; 8 pages.

* cited by examiner

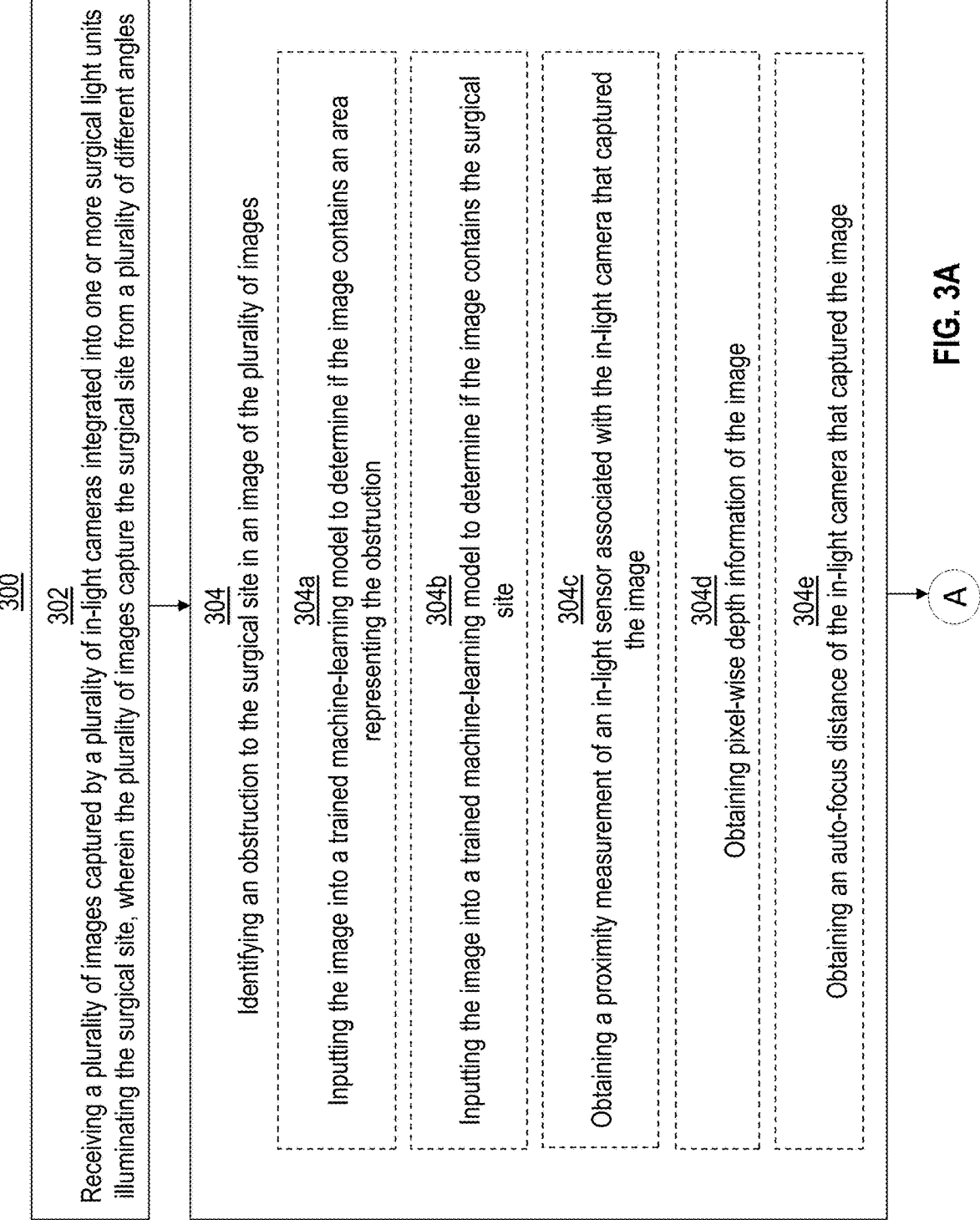

300

302
Receiving a plurality of images captured by a plurality of in-light cameras integrated into one or more surgical light units illuminating the surgical site, wherein the plurality of images capture the surgical site from a plurality of different angles 304
Identifying an obstruction to the surgical site in an image of the plurality of images 304a
Inputting the image into a trained machine-learning model to determine if the image contains an area representing the obstruction 304b
Inputting the image into a trained machine-learning model to determine if the image contains the surgical site 304c
Obtaining a proximity measurement of an in-light sensor associated with the in-light camera that captured the image 304d
Obtaining pixel-wise depth information of the image 304e
Obtaining an auto-focus distance of the in-light camera that captured the image

306
Responsive to identifying the obstruction, generating a composite image based on a set of the plurality of images, wherein the composite image excludes the obstruction 308
Displaying the composite image as the intraoperative image of the surgical site

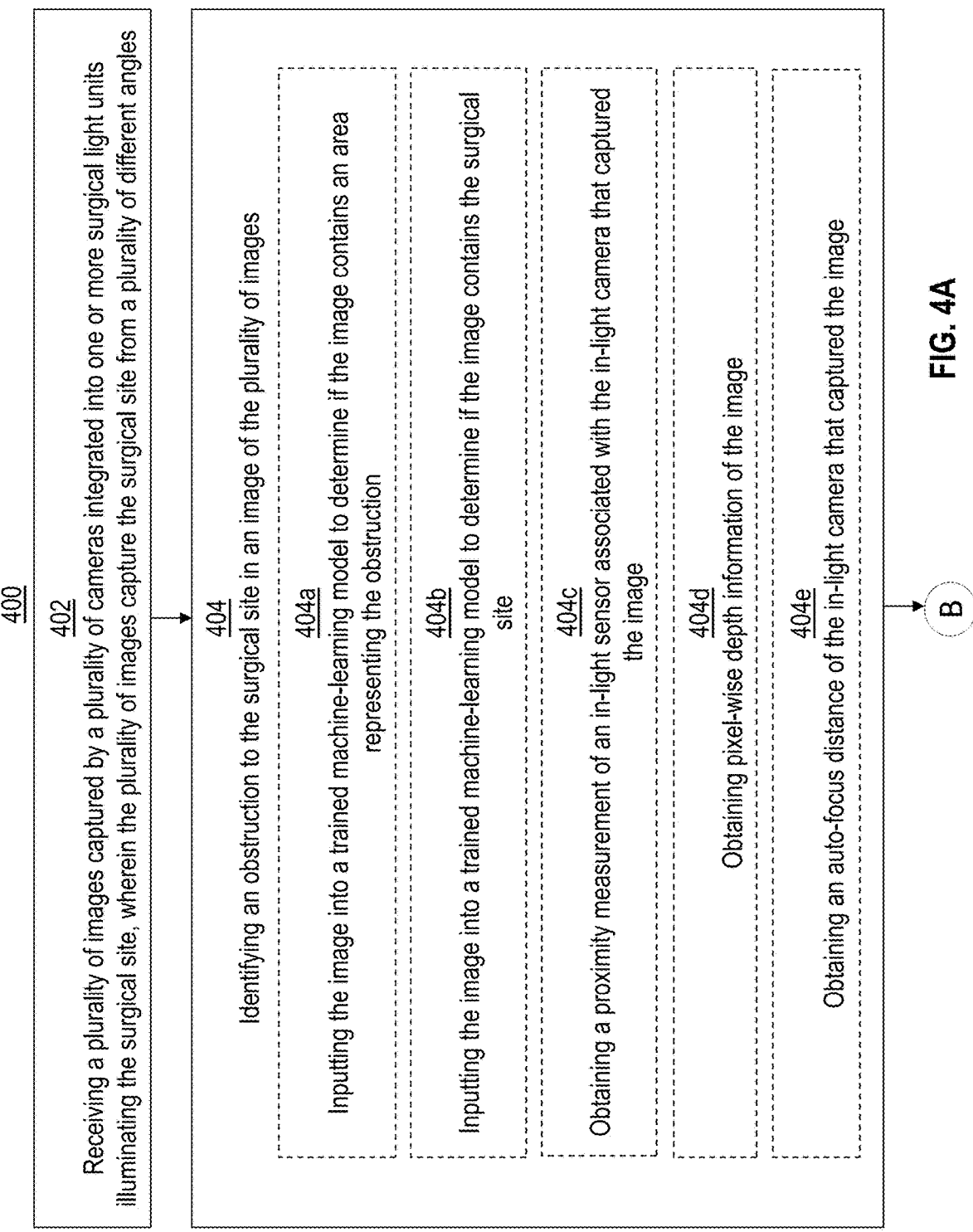

402
Receiving a plurality of images captured by a plurality of cameras integrated into one or more surgical light units illuminating the surgical site, wherein the plurality of images capture the surgical site from a plurality of different angles 404
Identifying an obstruction to the surgical site in an image of the plurality of images 404a
Inputting the image into a trained machine-learning model to determine if the image contains an area representing the obstruction 404b
Inputting the image into a trained machine-learning model to determine if the image contains the surgical site 404c
Obtaining a proximity measurement of an in-light sensor associated with the in-light camera that captured the image 404d
Obtaining pixel-wise depth information of the image 404e
Obtaining an auto-focus distance of the in-light camera that captured the image

B

B

406
In accordance with a determination that the image includes the obstruction, selecting another image from the plurality of images, wherein the selected image excludes the obstruction 408
Displaying the selected image as the intraoperative image of the surgical site

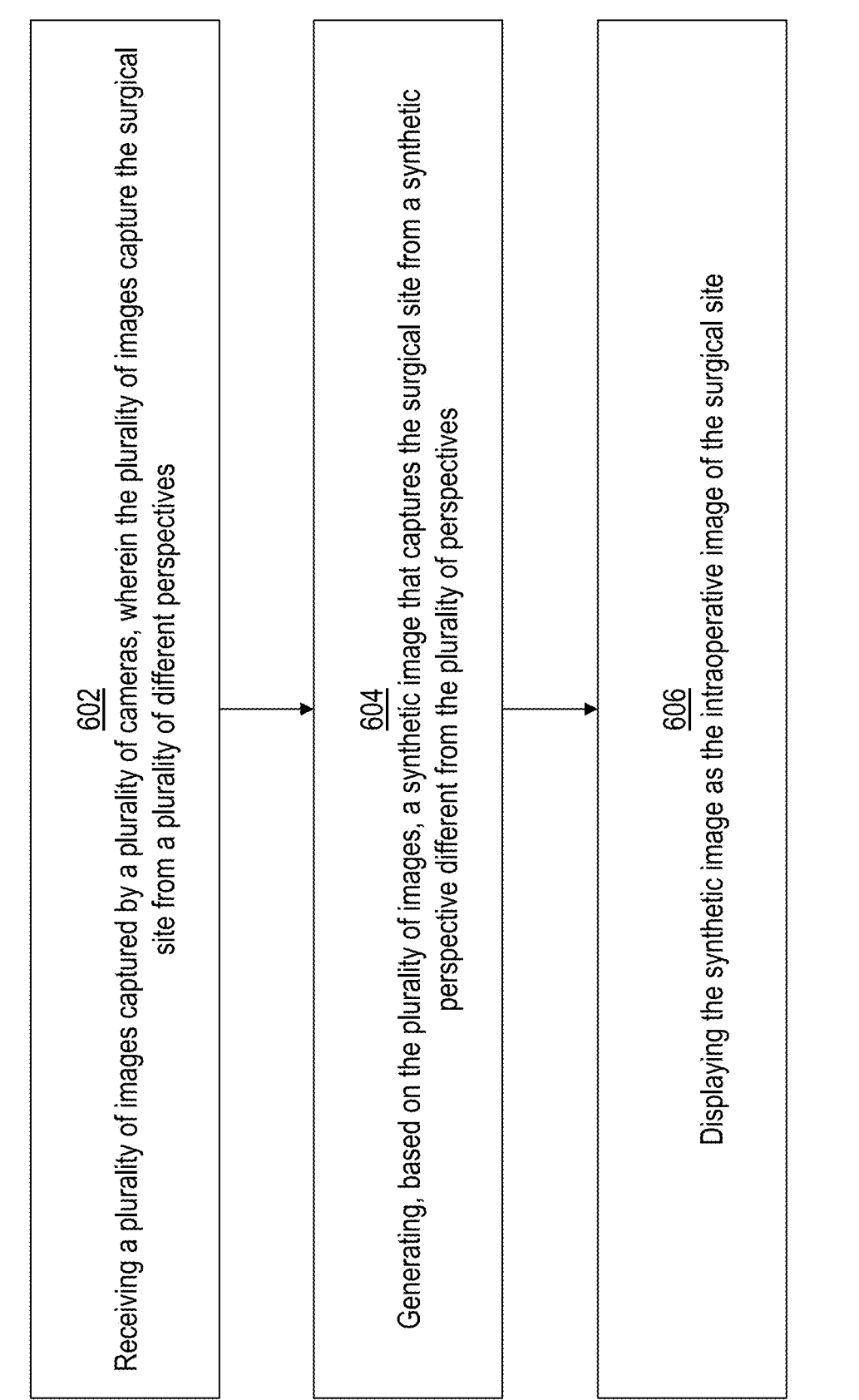

600

602
Receiving a plurality of images captured by a plurality of cameras, wherein the plurality of images capture the surgical site from a plurality of different perspectives 604
Generating, based on the plurality of images, a synthetic image that captures the surgical site from a synthetic perspective different from the plurality of perspectives 606
Displaying the synthetic image as the intraoperative image of the surgical site

FIG. 6

SYSTEMS AND METHODS FOR DISPLAYING INTRAOPERATIVE IMAGE DATA

CROSS-REFERENCE TO RELATED APPLICATIONS

This application claims the benefit of U.S. Provisional Application No. 63/263,819, filed Nov. 9, 2021, the entire contents of which are hereby incorporated by reference herein.

FIELD

The present invention relates to image processing techniques, and in particular, to techniques for generating and displaying intraoperative images of a surgical site (e.g., during open field surgery).

BACKGROUND

Surgical lights are used in operating rooms to provide relatively high intensity light to a target surgical site for illuminating the target surgical site during open field surgery. The target surgical site may be illuminated by the one or more surgical lights for direct observation by the surgeon. Surgical lights are typically mounted on suspension arms that enable users to adjust the position and orientation of the surgical lights. Surgical lights often have a centrally located handle that a user can grasp to reposition the surgical light.

A surgical light may include an in-light camera embedded in the same housing as the light source(s) of the surgical light. The in-light camera can capture images and videos during surgical procedures. However, the images and videos captured by in-light cameras are not relied upon by surgeons to aid surgical procedures. Instead, they are primarily used for observation, education, and training purposes outside the operating room. This is because surgical lights are typically placed close to and above the surgeon's head to provide optimal illumination of the target surgical site. Thus, the surgeon's head or body parts may often obstruct the target surgical site in the field of view of the in-light cameras, thus rendering the images and videos to be of limited value to surgeons during surgical procedures.

SUMMARY

An exemplary method of displaying an intraoperative image of a surgical site comprises: receiving a plurality of images captured by a plurality of in-light cameras integrated into one or more surgical light units illuminating the surgical site, wherein the plurality of images capture the surgical site from a plurality of different perspectives; identifying an obstruction to the surgical site in an image of the plurality of images; responsive to identifying the obstruction, generating a composite image based on a set of the plurality of images, wherein the composite image excludes the obstruction; and displaying the composite image as the intraoperative image of the surgical site.

In some examples, the composite image is generated such that the surgical site is generally centrally positioned within the frame of the composite image.

In some examples, the plurality of images is captured at a same time.

In some examples, the plurality of in-light cameras is integrated into a single surgical light unit.

In some examples, the plurality of in-light cameras comprises a central camera and a set of peripheral cameras surrounding the central camera.

In some examples, the plurality of in-light cameras comprises: a first set of one or more in-light cameras integrated into a first surgical light unit illuminating the surgical site; and a second set of one or more in-light cameras integrated into a second surgical light unit illuminating the surgical site.

In some examples, the method further comprises simultaneously displaying a first view corresponding to the first surgical light unit and a second view corresponding to the second surgical light unit, wherein the composite image is included in one of the first view and the second view.

In some examples, the obstruction includes a surgeon's head or a surgeon's body and does not include surgical tools or a surgeon's hand at the surgical site.

In some examples, detecting the obstruction to the surgical site in the image of the plurality of images comprises: inputting the image into a trained machine-learning model to determine if the image contains an area representing the obstruction.

In some examples, the trained machine-learning model is configured to receive an input image and detect an area in the input image as blocking the surgical site.

In some examples, the machine-learning model is trained using a plurality of labeled training images.

In some examples, detecting the obstruction to the surgical site in the image comprises: inputting the image into a trained machine-learning model to determine if the image contains the surgical site; and if the image does not contain the surgical site, detecting the obstruction in the image.

In some examples, the trained machine-learning model is configured to receive an input image and detect an area in the input image as the surgical site.

In some examples, the machine-learning model is trained using a plurality of labeled training images.

In some examples, each in-light camera of the plurality of in-light cameras is associated with an in-light sensor in the same surgical light unit.

In some examples, detecting the obstruction to the surgical site in the image comprises: obtaining a proximity measurement of an in-light sensor associated the in-light camera that captured the image; comparing the proximity measurement with a predefined threshold; and based on the comparison, determining whether the image includes the obstruction.

In some examples, the in-light sensor comprises a capacitive sensor, a Doppler sensor, an inductive sensor, a magnetic sensor, an optical sensor, a LiDAR sensor, a sonar sensor, an ultrasonic sensor, a radar sensor, or a hall effect sensor.

In some examples, detecting the obstruction to the surgical site in the image comprises obtaining an auto-focus distance of the in-light camera that captured the image; comparing the auto-focus distance with a predefined threshold; and based on the comparison, determining whether the image includes the obstruction.

In some examples, detecting the obstruction to the surgical site in the image comprises: obtaining pixel-wise depth information of the image; based on the pixel-wise depth information, determining whether the image includes the obstruction.

In some examples, generating a composite image based on a set of the plurality of images comprises: identifying in the image an area representing the obstruction; and replacing pixels in the area with pixels from the set of images.

In some examples, at least one in-light camera of the plurality of in-light cameras comprises a fisheye lens.

In some examples, the method further comprises: performing correction to an image captured by the at least one in-light camera to compensate for distortion caused by the fisheye lens.

In some examples, the method further comprises: automatically reorienting one or more of the plurality of in-light cameras.

In some examples, the method further comprises: reorienting one or more of the plurality of in-light cameras based on a user input.

In some examples, the method further comprises: inputting the composite image into a trained machine-learning model to detect an issue; and outputting an alert based on the issue.

In some examples, the issue comprises one or more of peripheral tissue damage, incorrect procedures, undiagnosed issues, and retained surgical bodies.

In some examples, the composite image is displayed as part of a video image transmission stream.

An exemplary method of displaying an intraoperative image of a surgical site comprises: receiving a plurality of images captured by a plurality of cameras integrated into one or more surgical light units illuminating the surgical site, wherein the plurality of images capture the surgical site from a plurality of different perspectives; inputting an image of the plurality of images into a trained machine-learning model to determine if the image includes an obstruction to the surgical site; in accordance with a determination that the image includes the obstruction, selecting another image from the plurality of images, wherein the selected image excludes the obstruction; and displaying the selected image as the intraoperative image of the surgical site.

In some examples, at least one camera of the plurality of cameras is located outside a surgical light unit.

In some examples, the selected image is an image from the plurality of images in which the surgical site is centrally positioned within the camera's field of view.

In some examples, the plurality of images is captured at a same time.

In some examples, the plurality of in-light cameras is integrated into a single surgical light unit.

In some examples, the plurality of in-light cameras comprises a central camera and a set of peripheral cameras surrounding the central camera, and wherein the inputted image is captured by the central camera and the selected image is captured by a peripheral camera in the set of peripheral cameras.

In some examples, the plurality of in-light cameras comprises: a first set of one or more in-light cameras integrated into a first surgical light unit illuminating the surgical site; and a second set of one or more in-light cameras integrated into a second surgical light unit illuminating the surgical site.

In some examples, the method further comprises simultaneously displaying a first view corresponding to the first surgical light unit and a second view corresponding to the second surgical light unit, wherein the selected image is included in one of the first view and the second view.

In some examples, the obstruction includes a surgeon's head or a surgeon's body.

In some examples, the obstruction does not include surgical tools or a surgeon's hand at the surgical site.

In some examples, determining if the image includes the obstruction to the surgical site comprises: inputting the image into the trained machine-learning model to determine if the image contains an area representing the obstruction; and if the image contains the area representing the obstruction, determining that the image includes the obstruction.

In some examples, the trained machine-learning model is configured to receive an input image and detect an area in the input image as blocking the surgical site.

In some examples, the machine-learning model is trained using a plurality of labeled training images.

In some examples, determining if the image includes the obstruction to the surgical site comprises: inputting the image into the trained machine-learning model to determine if the image contains the surgical site; and if the image does not contain the surgical site, determining that the image includes the obstruction.

In some examples, the trained machine-learning model is configured to receive an input image and detect an area in the input image as the surgical site.

In some examples, the machine-learning model is trained using a plurality of labeled training images.

In some examples, the method further comprises automatically reorienting one or more of the plurality of in-light cameras.

In some examples, the method further comprises reorienting one or more of the plurality of in-light cameras based on a user input.

In some examples, the method further comprises inputting the selected image into a trained machine-learning model to detect an issue; and outputting an alert based on the issue.

In some examples, the issue comprises one or more of peripheral tissue damage, incorrect procedures, undiagnosed issues, and retained surgical bodies.

In some examples, the selected image is displayed as part of a video image transmission stream.

An exemplary system for displaying an intraoperative image of a surgical site comprises: a display; one or more processors; a memory; and one or more programs, wherein the one or more programs are stored in the memory and configured to be executed by the one or more processors, the one or more programs including instructions for: receiving a plurality of images captured by a plurality of in-light cameras integrated into one or more surgical light units illuminating the surgical site, wherein the plurality of images capture the surgical site from a plurality of different perspectives; identifying an obstruction to the surgical site in an image of the plurality of images; responsive to identifying the obstruction, generating a composite image based on a set of the plurality of images, wherein the composite image excludes the obstruction; and displaying the composite image as the intraoperative image of the surgical site.

In some examples, the plurality of images is captured at a same time.

In some examples, the plurality of in-light cameras is integrated into a single surgical light unit.

In some examples, the plurality of in-light cameras comprises a central camera and a set of peripheral cameras surrounding the central camera.

In some examples, the plurality of in-light cameras comprises: a first set of one or more in-light cameras integrated into a first surgical light unit illuminating the surgical site; and a second set of one or more in-light cameras integrated into a second surgical light unit illuminating the surgical site.

In some examples, the one or more programs further include instructions for: simultaneously displaying a first view corresponding to the first surgical light unit and a second view corresponding to the second surgical light unit, wherein the composite image is included in one of the first view and the second view.

In some examples, the obstruction includes a surgeon's head or a surgeon's body and does not include surgical tools or a surgeon's hand at the surgical site.

In some examples, detecting the obstruction to the surgical site in the image of the plurality of images comprises: inputting the image into a trained machine-learning model to determine if the image contains an area representing the obstruction.

In some examples, the trained machine-learning model is configured to receive an input image and detect an area in the input image as blocking the surgical site.

In some examples, the machine-learning model is trained using a plurality of labeled training images.

In some examples, detecting the obstruction to the surgical site in the image comprises: inputting the image into a trained machine-learning model to determine if the image contains the surgical site; and if the image does not contain the surgical site, detecting the obstruction in the image.

In some examples, the trained machine-learning model is configured to receive an input image and detect an area in the input image as the surgical site.

In some examples, the machine-learning model is trained using a plurality of labeled training images.

In some examples, each in-light camera of the plurality of in-light cameras is associated with an in-light sensor in the same surgical light unit.

In some examples, detecting the obstruction to the surgical site in the image comprises: obtaining a proximity measurement of an in-light sensor associated the in-light camera that captured the image; comparing the proximity measurement with a predefined threshold; and based on the comparison, determining whether the image includes the obstruction.

In some examples, the in-light sensor comprises a capacitive sensor, a Doppler sensor, an inductive sensor, a magnetic sensor, an optical sensor, a LiDAR sensor, a sonar sensor, an ultrasonic sensor, a radar sensor, or a hall effect sensor.

In some examples, detecting the obstruction to the surgical site in the image comprises: obtaining an auto-focus distance of the in-light camera that captured the image; comparing the auto-focus distance with a predefined threshold; and based on the comparison, determining whether the image includes the obstruction.

In some examples, detecting the obstruction to the surgical site in the image comprises: obtaining pixel-wise depth information of the image; based on the pixel-wise depth information, determining whether the image includes the obstruction.

In some examples, generating a composite image based on a set of the plurality of images comprises: identifying in the image an area representing the obstruction; and replacing pixels in the area with pixels from the set of images.

In some examples, at least one in-light camera of the plurality of in-light cameras comprises a fisheye lens.

In some examples, the one or more programs further include instructions for: performing correction to an image captured by the at least one in-light camera to compensate for distortion caused by the fisheye lens.

In some examples, the one or more programs further include instructions for: automatically reorienting one or more of the plurality of in-light cameras.

In some examples, the one or more programs further include instructions for: reorienting one or more of the plurality of in-light cameras based on a user input.

In some examples, the one or more programs further include instructions for: inputting the composite image into a trained machine-learning model to detect an issue; and outputting an alert based on the issue.

In some examples, the issue comprises one or more of peripheral tissue damage, incorrect procedures, undiagnosed issues, and retained surgical bodies.

In some examples, the composite image is displayed as part of a video image transmission stream.

An exemplary system of displaying an intraoperative image of a surgical site comprises: a display; one or more processors; a memory; and one or more programs, wherein the one or more programs are stored in the memory and configured to be executed by the one or more processors, the one or more programs including instructions for: receiving a plurality of images captured by a plurality of cameras, wherein the plurality of images capture the surgical site from a plurality of different perspectives; inputting an image of the plurality of images into a trained machine-learning model to determine if the image includes an obstruction to the surgical site; in accordance with a determination that the image includes the obstruction, selecting another image from the plurality of images, wherein the selected image excludes the obstruction; and displaying the selected image as the intraoperative image of the surgical site.

In some examples, the plurality of images is captured at a same time.

In some examples, the plurality of cameras is integrated into a single surgical light unit.

In some examples, the plurality of cameras comprises a central camera and a set of peripheral cameras surrounding the central camera, and wherein the inputted image is captured by the central camera and the selected image is captured by a peripheral camera in the set of peripheral cameras.

In some examples, the plurality of cameras comprises: a first set of one or more in-light cameras integrated into a first surgical light unit illuminating the surgical site; and a second set of one or more in-light cameras integrated into a second surgical light unit illuminating the surgical site.

In some examples, the one or more programs further include instructions for: simultaneously displaying a first view corresponding to the first surgical light unit and a second view corresponding to the second surgical light unit, wherein the selected image is included in one of the first view and the second view.

In some examples, the obstruction includes a surgeon's head or a surgeon's body.

In some examples, the obstruction does not include surgical tools or a surgeon's hand at the surgical site.

In some examples, determining if the image includes the obstruction to the surgical site comprises: inputting the image into the trained machine-learning model to determine if the image contains an area representing the obstruction; and if the image contains the area representing the obstruction, determining that the image includes the obstruction.

In some examples, the trained machine-learning model is configured to receive an input image and detect an area in the input image as blocking the surgical site.

In some examples, the machine-learning model is trained using a plurality of labeled training images.

In some examples, determining if the image includes the obstruction to the surgical site comprises inputting the image into the trained machine-learning model to determine if the image contains the surgical site; and if the image does not contain the surgical site, determining that the image includes the obstruction.

In some examples, the trained machine-learning model is configured to receive an input image and detect an area in the input image as the surgical site.

In some examples, the machine-learning model is trained using a plurality of labeled training images.

In some examples, the one or more programs further include instructions for: automatically reorienting one or more of the plurality of cameras.

In some examples, the one or more programs further include instructions for: reorienting one or more of the plurality of cameras based on a user input.

In some examples, the one or more programs further include instructions for: inputting the selected image into a trained machine-learning model to detect an issue; and outputting an alert based on the issue.

In some examples, the issue comprises one or more of peripheral tissue damage, incorrect procedures, undiagnosed issues, and retained surgical bodies.

In some examples, the selected image is displayed as part of a video image transmission stream.

An exemplary method of displaying an intraoperative image of a surgical site comprises: receiving a plurality of images captured by a plurality of cameras, wherein the plurality of images capture the surgical site from a plurality of different perspectives; generating, based on the plurality of images, a synthetic image that captures the surgical site from a synthetic perspective different from the plurality of perspectives; and displaying the synthetic image as the intraoperative image of the surgical site.

In some examples, at least one camera of the plurality of cameras is located outside a surgical light unit.

In some examples, the plurality of images is captured at a same time.

In some examples, the plurality of cameras is integrated into a single surgical light unit.

In some examples, the plurality of cameras comprises a set of peripheral cameras, and wherein the synthetic perspective is from the center of the single surgical light unit.

In some examples, the plurality of cameras comprises: a first set of one or more in-light cameras integrated into a first surgical light unit illuminating the surgical site; and a second set of one or more in-light cameras integrated into a second surgical light unit illuminating the surgical site.

In some examples, the plurality of cameras includes two cameras having different focal lengths.

In some examples, the two cameras comprise a wide angle lens camera and a telephoto lens camera.

In some examples, the synthetic image is a medium focal length image.

In some examples, the method further comprises identifying an obstruction to the surgical site in an image of the plurality of images, wherein the synthetic image is generated responsive to identifying the obstruction.

In some examples, the obstruction includes a surgeon's head or a surgeon's body and does not include surgical tools or a surgeon's hand at the surgical site.

In some examples, detecting the obstruction to the surgical site in the image of the plurality of images comprises: inputting the image into a trained machine-learning model to determine if the image contains an area representing the obstruction.

In some examples, the trained machine-learning model is configured to receive an input image and detect an area in the input image as blocking the surgical site.

In some examples, detecting the obstruction to the surgical site in the image comprises: inputting the image into a trained machine-learning model to determine if the image contains the surgical site; and if the image does not contain the surgical site, detecting the obstruction in the image.

In some examples, the trained machine-learning model is configured to receive an input image and detect an area in the input image as the surgical site.

In some examples, each in-light camera of the plurality of in-light cameras is associated with an in-light sensor in the same surgical light unit.

In some examples, detecting the obstruction to the surgical site in the image comprises: obtaining a proximity measurement of an in-light sensor associated the in-light camera that captured the image; comparing the proximity measurement with a predefined threshold; and based on the comparison, determining whether the image includes the obstruction.

In some examples, detecting the obstruction to the surgical site in the image comprises: obtaining an auto-focus distance of the in-light camera that captured the image; comparing the auto-focus distance with a predefined threshold; and based on the comparison, determining whether the image includes the obstruction.

In some examples, detecting the obstruction to the surgical site in the image comprises: obtaining pixel-wise depth information of the image; based on the pixel-wise depth information, determining whether the image includes the obstruction.

An exemplary system of displaying an intraoperative image of a surgical site comprises: a display; one or more processors; a memory; and one or more programs, wherein the one or more programs are stored in the memory and configured to be executed by the one or more processors, the one or more programs including instructions for: receiving a plurality of images captured by a plurality of cameras, wherein the plurality of images capture the surgical site from a plurality of different perspectives; generating, based on the plurality of images, a synthetic image that captures the surgical site from a synthetic perspective different from the plurality of perspectives; and displaying the synthetic image as the intraoperative image of the surgical site.

In some examples, the plurality of images is captured at a same time.

In some examples, the plurality of cameras is integrated into a single surgical light unit.

In some examples, the plurality of cameras comprises a set of peripheral cameras, and wherein the synthetic perspective is from the center of the single surgical light unit.

In some examples, the plurality of cameras comprises: a first set of one or more in-light cameras integrated into a first surgical light unit illuminating the surgical site; and a second set of one or more in-light cameras integrated into a second surgical light unit illuminating the surgical site.

In some examples, the plurality of cameras includes two cameras having different focal lengths.

In some examples, the two cameras comprise a wide angle lens camera and a telephoto lens camera.

In some examples, the synthetic image is a medium focal length image.

In some examples, the one or more programs further comprise instructions for identifying an obstruction to the surgical site in an image of the plurality of images, wherein the synthetic image is generated responsive to identifying the obstruction.

In some examples, the obstruction includes a surgeon's head or a surgeon's body and does not include surgical tools or a surgeon's hand at the surgical site.

In some examples, detecting the obstruction to the surgical site in the image of the plurality of images comprises: inputting the image into a trained machine-learning model to determine if the image contains an area representing the obstruction.

In some examples, the trained machine-learning model is configured to receive an input image and detect an area in the input image as blocking the surgical site.

In some examples, detecting the obstruction to the surgical site in the image comprises: inputting the image into a trained machine-learning model to determine if the image contains the surgical site; and if the image does not contain the surgical site, detecting the obstruction in the image.

In some examples, the trained machine-learning model is configured to receive an input image and detect an area in the input image as the surgical site.

In some examples, each in-light camera of the plurality of in-light cameras is associated with an in-light sensor in the same surgical light unit.

In some examples, detecting the obstruction to the surgical site in the image comprises: obtaining a proximity measurement of an in-light sensor associated the in-light camera that captured the image; comparing the proximity measurement with a predefined threshold; and based on the comparison, determining whether the image includes the obstruction.

In some examples, detecting the obstruction to the surgical site in the image comprises: obtaining an auto-focus distance of the in-light camera that captured the image; comparing the auto-focus distance with a predefined threshold; and based on the comparison, determining whether the image includes the obstruction.

In some examples, detecting the obstruction to the surgical site in the image comprises: obtaining pixel-wise depth information of the image; based on the pixel-wise depth information, determining whether the image includes the obstruction.

A non-transitory computer-readable storage medium stores one or more programs, the one or more programs comprising instructions, which when executed by one or more processors of an electronic device, cause the electronic device to perform any of the methods described herein.

BRIEF DESCRIPTION OF THE FIGURES

FIGS. 3A and 3B illustrate an exemplary process for displaying an intraoperative image of a surgical site, in accordance with some examples.

FIGS. 4A and 4B illustrate an exemplary process for displaying an intraoperative image of a surgical site, in accordance with some examples.

FIG. 6 illustrate an exemplary process for displaying an intraoperative image of a surgical site, in accordance with some examples.

DETAILED DESCRIPTION

Figure 1A:
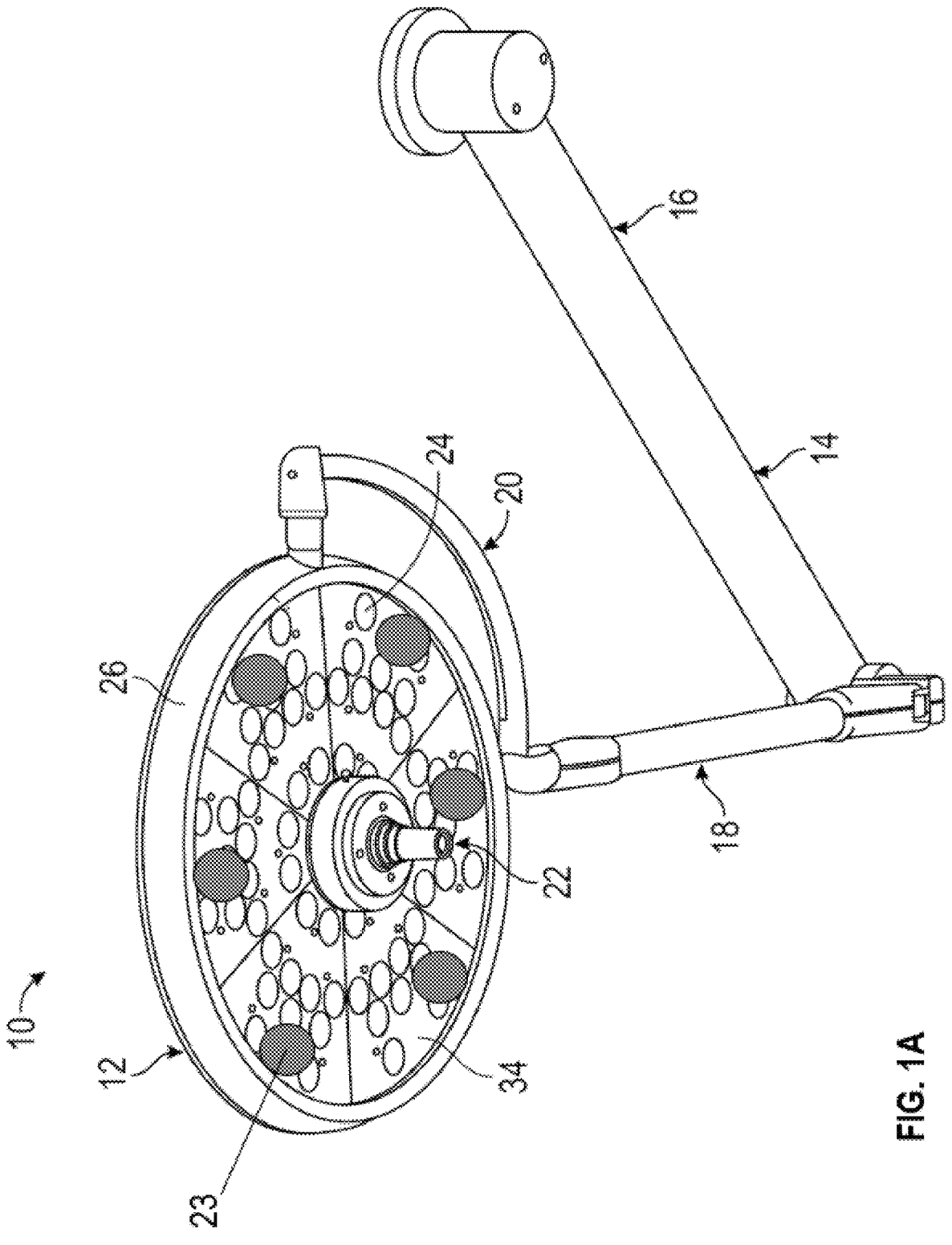
FIG. 1A illustrates an exemplary surgical lighting system, according to various examples.

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Disclosed herein are methods, systems, electronic devices, apparatuses, and non-transitory storage media for generating and displaying intraoperative images of a surgical site. In some examples, the intraoperative images are generated based on image data captured by in-light cameras embedded in one or more surgical lights. Because surgical lights are typically placed close to and above the surgeon's head to provide optimal illumination of the target surgical site, the surgeon's head or body parts would often obstruct the surgical area in the field of view of the in-light cameras. Techniques described herein can be used to process image data captured by in-light cameras to eliminate or reduce the obstruction. For example, the obstruction can be eliminated from an image based on image data captured by other in-light cameras from different perspectives at the same time. As another example, the obstruction can be eliminated or reduced by selecting a least-obstructed image for display out of many images captured by the various in-light cameras. Thus, techniques described herein can allow in-light cameras to provide a continuous, unobstructed field of view of the target surgical site, thus making a wide variety of applications possible. For example, the continuous, unobstructed view of the target surgical site can be provided on a display to guide the surgeons during a surgical procedure. Further, the image data can be further analyzed to track surgical tools, analyze the operation, and/or identify issues (e.g., peripheral tissue damage, incorrect procedures, undiagnosed issues, retained surgical bodies). In some examples, the analyses can be performed using machine-learning models.

An exemplary method of displaying an intraoperative image of a surgical site comprises: receiving a plurality of images captured by a plurality of cameras integrated into one or more surgical light units illuminating the surgical site, wherein the plurality of images capture the surgical site from a plurality of different perspectives; inputting an image of the plurality of images into a trained machine-learning model to determine if the image includes an obstruction to the surgical site; in accordance with a determination that the image includes the obstruction, selecting another image from the plurality of images, wherein the selected image excludes the obstruction; and displaying the selected image as the intraoperative image of the surgical site. In some examples, the image is selected by a user or based on preferences of the user.

An exemplary system of displaying an intraoperative image of a surgical site comprises: a display; one or more processors; a memory; and one or more programs, wherein the one or more programs are stored in the memory and configured to be executed by the one or more processors, the one or more programs including instructions for: receiving a plurality of images captured by a plurality of cameras, wherein the plurality of images capture the surgical site from a plurality of different perspectives; inputting an image of the plurality of images into a trained machine-learning model to determine if the image includes an obstruction to the surgical site; in accordance with a determination that the image includes the obstruction, selecting another image from the plurality of images, wherein the selected image excludes the obstruction; and displaying the selected image as the intraoperative image of the surgical site.

An exemplary method of displaying an intraoperative image of a surgical site comprises: receiving a plurality of images captured by a plurality of in-light cameras integrated into one or more surgical light units illuminating the surgical site, wherein the plurality of images capture the surgical site from a plurality of different perspectives; identifying an obstruction to the surgical site in an image of the plurality of images; responsive to identifying the obstruction, generating a composite image based on a set of the plurality of images, wherein the composite image excludes the obstruction; and displaying the composite image as the intraoperative image of the surgical site. In some examples, the composite image can be generated using portions of the obstructed field of view image and a portion of an image from an unobstructed field of view image, as described herein.

An exemplary system for displaying an intraoperative image of a surgical site comprises: a display; one or more processors; a memory; and one or more programs, wherein the one or more programs are stored in the memory and configured to be executed by the one or more processors, the one or more programs including instructions for: receiving a plurality of images captured by a plurality of in-light cameras integrated into one or more surgical light units illuminating the surgical site, wherein the plurality of images capture the surgical site from a plurality of different perspectives; identifying an obstruction to the surgical site in an image of the plurality of images; responsive to identifying the obstruction, generating a composite image based on a set of the plurality of images, wherein the composite image excludes the obstruction; and displaying the composite image as the intraoperative image of the surgical site.

In the following description of the various examples, reference is made to the accompanying drawings, in which are shown, by way of illustration, specific examples that can be practiced. It is to be understood that other examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1A illustrates a surgical lighting system 10, according to various examples. The surgical lighting system 10 is configured to be positioned within a room (e.g., an operating room) for providing illumination to a desired area of the room. While the surgical light system 10 can be placed within an operating room for illuminating a patient for a surgical procedure, the surgical light system 10 can also be placed in any area wherein increased light at a targeted location is desired. The surgical light system 10 includes a surgical light 12 and a suspension arm 14 for connecting the surgical light 12 to a static or movable structure within the operating room. For example, the suspension arm 14 can be directly connected to a suspension system connected to a wall or ceiling of the operating room, can be connected to a further arm assembly (not shown) or suspension system directly connected to a wall or ceiling of the operating room, or can be directly or indirectly connected to a movable assembly located within the operating room.

The surgical light 12 includes a housing 26 and a plurality of light sources (e.g., light source 24). Each light source 24 comprises a light-producing element (e.g., LED) and light directing optics. The housing 26 includes a circular face glass 34 covering the at least one light source 28. Housings for light assemblies and the light sources and optics therein are well known to those skilled in the art. For example, the housing, light source and optics can be those of U.S. Patent Application Publication No. 2014/0268751 entitled MEDICAL LIGHT WITH BEAM REDIRECTING OPTICS, the entire contents of which are incorporated herein by reference. The light sources of the surgical light, according to various examples, can include any type of light emitter, such as incandescent (halogen lamp or a tungsten filament), discharge lamp, solid state, laser, or fluorescent light emitters. In some examples, emitters of the first and second light sources include one or more types of solid state light emitters such as one or more types of light-emitting diodes (LEDs), organic light-emitting diodes (OLED), superluminescent diodes (SLD), or polymer light-emitting diodes (PLED). In some examples, the light sources include narrow spectrum light emitters, such as red, green, and blue LEDs. In some examples, the light sources include broad spectrum light emitters, such as white light LEDs. In some examples, the light sources have the same type or different types of emitters.

The surgical light 12 can include one or more in-light cameras. In the depicted example, the surgical light 12 includes a plurality of in-light cameras including a central in-light camera 22 and multiple peripheral in-light cameras surrounding the central camera (e.g., camera 23) near the outer perimeter. The plurality of cameras can be installed inside or outside the housing 26 (e.g., on ceiling/wall). In some examples, the central camera is installed on a central handle assembly of the surgical light 12. In some examples, the plurality of in-light cameras are associated with varying characteristics (e.g. optics, image sensors, electronics, zoom range). Intraoperative images of the surgical site can be generated based on image data captured by the plurality of cameras using techniques described herein. In some examples, some or all of the imaging processing techniques described herein can be performed at a unit attached to the surgical light, as described herein.

In some examples, the video stream captured by the central camera can be displayed by default. If an obstruction is detected in the video stream captured by the central camera (e.g., in blocks 304 in FIG. 3A or 404 in FIG. 4A), the system can generate a composite image or select a different image using images captured by the peripheral cameras (e.g., in blocks 306 in FIG. 3B or 406 in FIG. 4B), as described in detail herein.

In some examples, the in-light cameras or the images captured by the in-light cameras are oriented to provide an optimal display to the surgeons. In some examples, orientation of the images can be controlled by orienting the in-light cameras manually and/or via actuator mechanisms (e.g., electric motors). In some examples, the images can be rotated digitally. For example, sensors in the surgical light can enable automatic reorientation of the images, depending on the orientation of the surgical light. For example, image can always be oriented with the top of the image aligned with the top of the surgical light. As another example, gyro sensors can be used to maintain orientation independently of the orientation of the surgical light. In some examples, twisting of a control handle (e.g. located at the center of the light head) can provide input to rotate the image via motorized or digital rotation. Control of camera orientation can also be remote, for example, via wall control, from integration platform (e.g. Switchpoint Infinity 3 Router, Switchpoint Infinity 4K Router, COR IP Routing System, COR Hub), or via remote control (e.g., Bluetooth, RF, IR, WiFi). In some examples, orientation of the peripheral cameras can be made adjustable to account for various focal distances (e.g., via motorized adjustment), depending on distance to working plane.

Figure 1B:
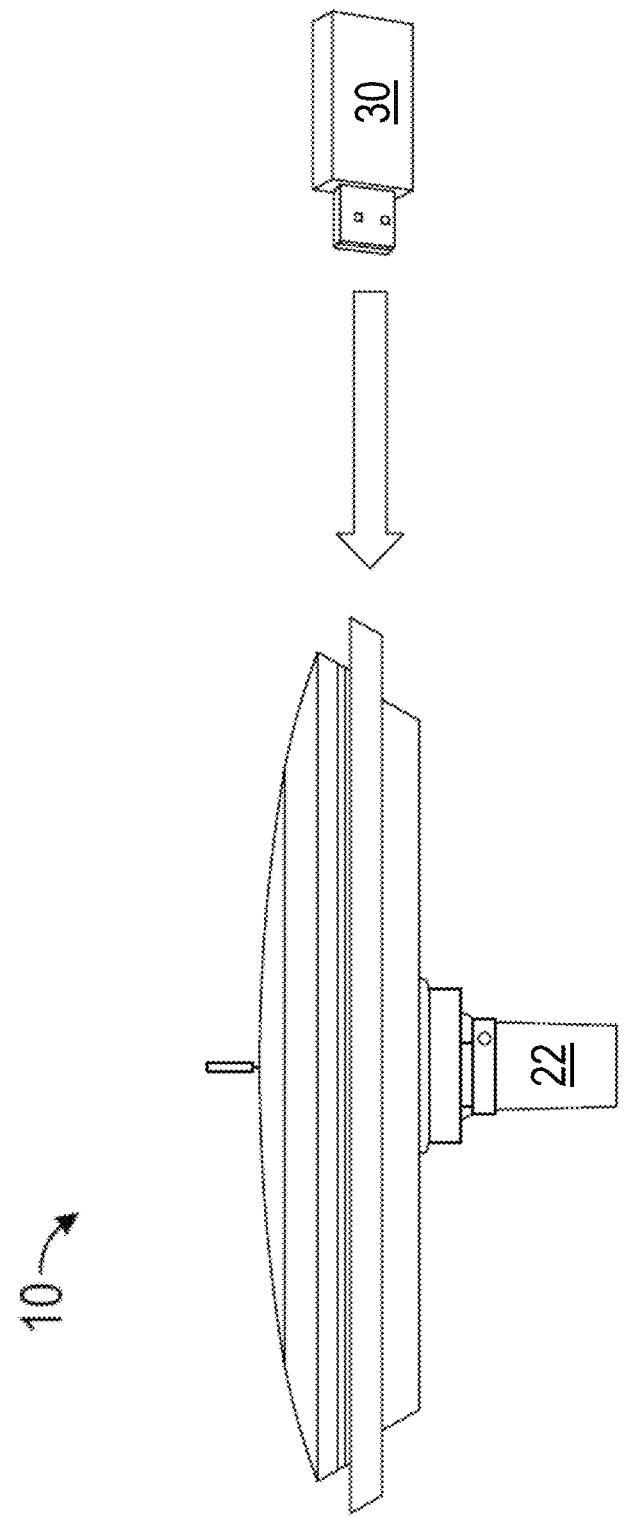
FIG. 1B illustrates an exemplary hardware dongle component of an exemplary surgical lighting system, according to various examples.

In some examples, the in-light cameras can be activated via a hardware dongle component as shown in FIG. 1B. The hardware dongle 30 can be required to activate some or all functionalities of the in-light cameras. In some examples, the dongle can contain some of the control, processing, or power electronics for performing the techniques described herein. In some examples, the dongle can be inserted into a slot of the surgical light (as shown in FIG. 1B) or a wall control panel to enable the features of in-light cameras. These features can also be enabled from a server upon a user request. In some examples, the dongle can contain one or more cameras. For example, the hardware dongle can include a camera that can act as the central camera as described herein.

In some examples, one or more of the in-light cameras comprise fisheye lenses to assist with obstruction removal. For example, fisheye lenses can be incorporated into some or all in-light cameras embedded in the surgical light. The fisheye lenses can be circular fisheye lenses. In some examples, the system performs software processing to eliminate curvilinear distortion and convert to a rectilinear perspective prior to the operations described with reference to FIGS. 3A, 3B, 4A, and 4B.

Turning back to FIG. 1A, the suspension arm 14 of the surgical light system 10 allows light from the surgical light 12 to be pointed at a certain area within the operating room (with the suspension system allowing the surgical light 12 to be selectively positioned within the operating room). The suspension arm 14 includes a first arm member 16 configured to be rotatably connected to a support (e.g., a ceiling), a second arm member 18 rotatably connected to the first arm member 16, and a curved link 20 extending between the second arm member 18 and the surgical light 12. The first arm member 16, the second arm member 18 and the curved link 20 allow the surgical light 12 to be moved to any desired location by grasping the central handle assembly extending from a face of the surgical light 12 and pulling, pushing and/or twisting the surgical light 12 to any desired location. While a specific suspension arm 14 is illustrated in FIG. 1A, any arm well known to those skilled in the art could be used to connect the surgical light 12 to the operating room structure or a movable assembly as discussed above (including one connected to multiple points on the side of the surgical light 12 and/or the rear surface thereof). The illustrated suspension arm 14 or any arm known to those skilled in the art allows for easy movement of the surgical light 12 into any position within the operating room and then maintaining the position of the surgical light 12 once released.

Figure 2A:
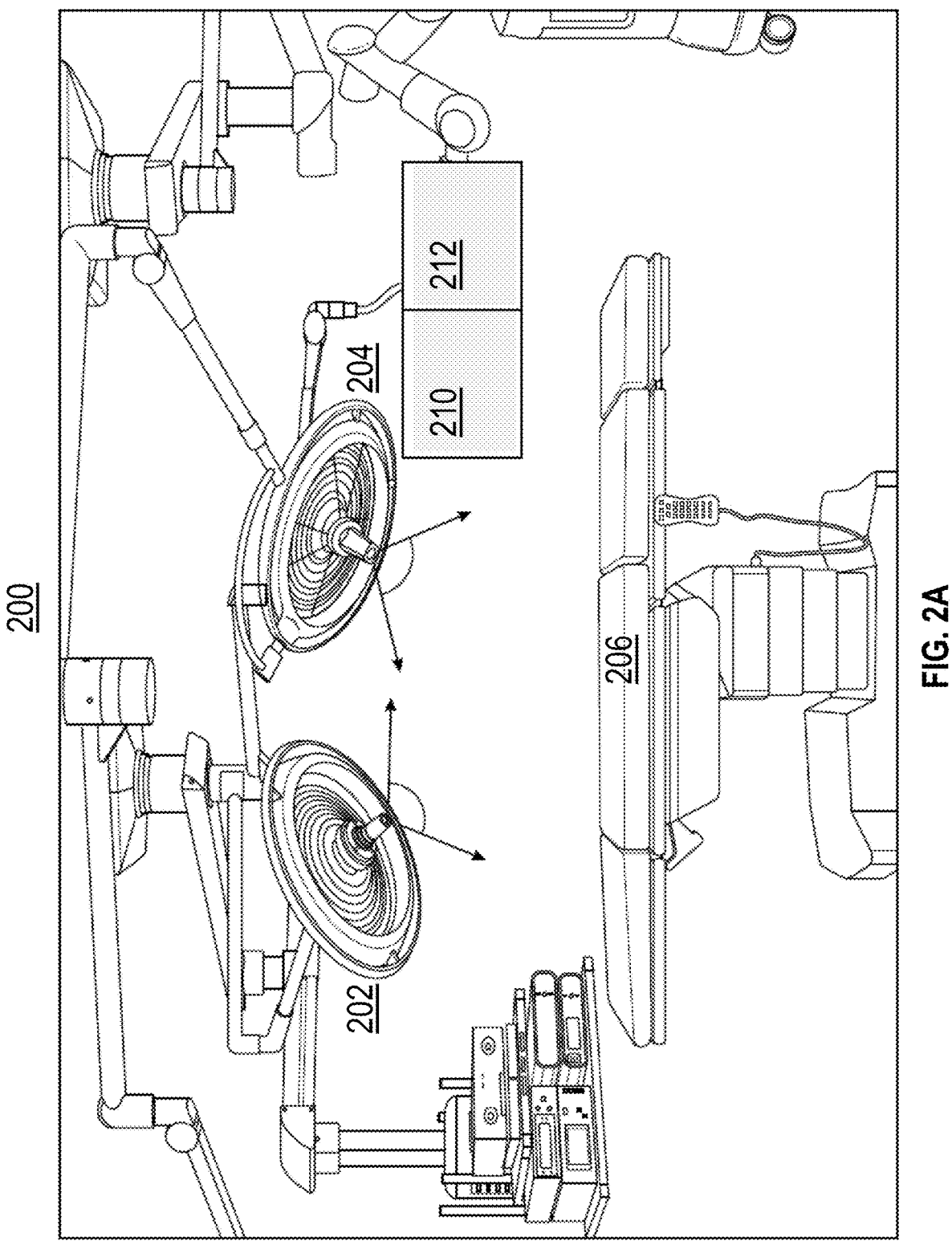
FIG. 2A illustrates a schematic representation of a surgical lighting system, according to some examples.

FIG. 2A illustrates a schematic representation of a surgical lighting system 200, according to some examples. The surgical lighting system 200 includes a first surgical light 202 and a second surgical light 204 for illuminating target tissue of a subject laying on the operating table 206 in an operating room. Each of the first surgical light 202 and the second surgical light 204 can be the surgical light 12 in FIG. 1A. As discussed above, each of the surgical lights may be mounted to a suspension arm assembly so that the surgical lights can be suspended above the operating table.

Each of the first surgical light 202 and the second surgical light 204 includes one or more in-light cameras for capturing image or video data. Data captured by the in-light cameras of the first surgical light 202 and the second surgical light 204 can be telecasted on displays 210 and 212 during surgical procedures. In some examples, each display is configured to display a video image transmission stream based on the data captured by the first surgical light 202, the data captured by the second surgical light 204, or a combination thereof using the techniques described herein.

Figure 2B:
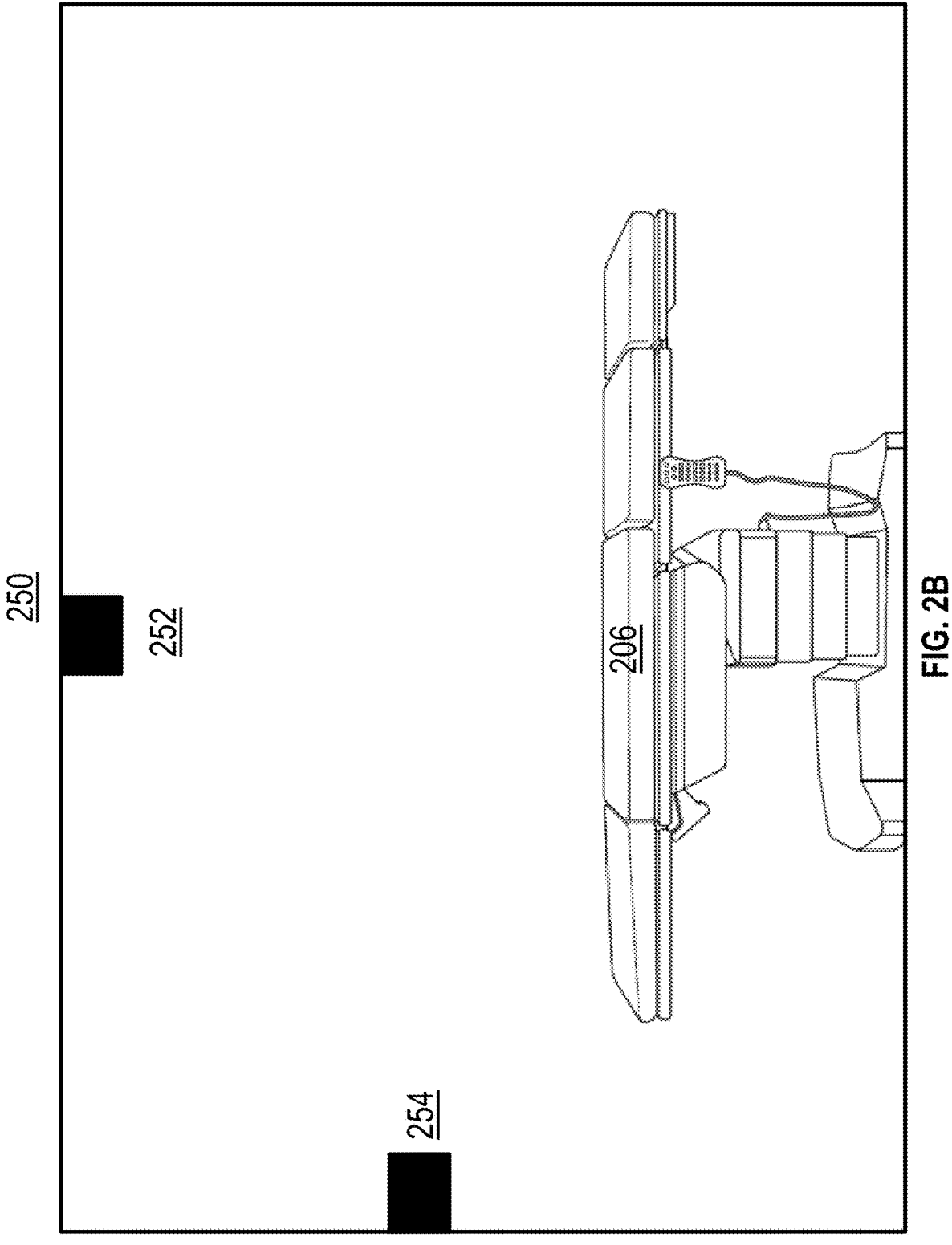
FIG. 2B illustrates a schematic representation of a surgical setup, according to some examples.

FIG. 2B illustrates a schematic representation of a surgical setup 250, according to some examples. Rather than being embedded in surgical lights, cameras 252 and 254 can be positioned in any area in the surgical suite to capture images of the surgical site 206. For example, the cameras can be embedded in the ceiling, on the walls, or in the corners of the surgical suite. As another example, the cameras can be individually supported from suspensions mounted to the ceiling or mobile roll stands. Images captured by cameras outside surgical lights can be used in any of the processes described herein, such as process 300, 400, and 600.

Figure 3B:
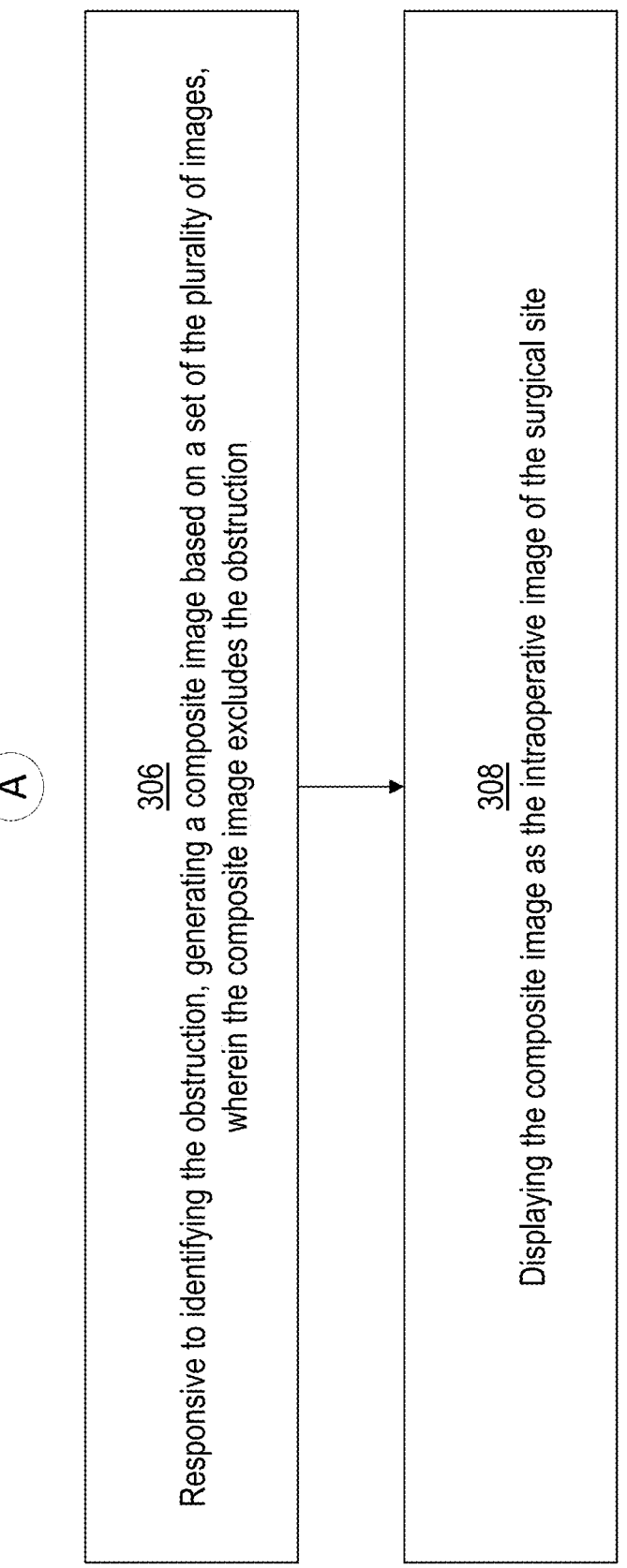

FIGS. 3A and 3B illustrate an exemplary process 300 for displaying an intraoperative image of a surgical site, in accordance with some examples. Process 300 is performed, for example, using one or more electronic devices implementing a software platform. In some examples, process 300 is performed using a client-server system, and the blocks of process 300 are divided up in any manner between the server and one or more client devices. In other examples, process 300 is performed using only a client device or only multiple client devices. In process 300, some blocks are, optionally, combined, the order of some blocks is, optionally, changed, and some blocks are, optionally, omitted. In some examples, additional steps may be performed in combination with the process 300. Accordingly, the operations as illustrated (and described in greater detail below) are exemplary by nature and, as such, should not be viewed as limiting.

At block 302, an exemplary system (e.g., one or more electronic devices) receives a plurality of images of the surgical site. In some examples, the images are captured by a plurality of in-light cameras integrated into one or more surgical light units (e.g., surgical light 12 in FIG. 1A) illuminating the surgical site. The plurality of images captures the surgical site from a plurality of different perspectives. In some examples, the plurality of images is captured at a same time.

In some examples, the plurality of in-light cameras is integrated into a single surgical light unit. For example, with reference to FIG. 1A, the plurality of in-light cameras can be two or more of the cameras installed in the surgical light 12, such as the central camera 22 and the peripheral cameras surrounding the central camera (e.g., camera 23). During a surgical procedure, the cameras within the surgical light 12 can capture a plurality of images of the surgical site at the same time from different perspectives. The plurality of images captures the surgical site from different perspectives because the cameras are at installed at different locations and have different orientations.

In some examples, the plurality of in-light cameras can be located in different light heads. For example, with reference to FIG. 2A, the plurality of cameras can comprise: a first set of one or more in-light cameras integrated into the first surgical light unit 202 illuminating the surgical site and a second set of one or more in-light cameras integrated into the second surgical light unit 204 illuminating the surgical site. During a surgical procedure, the cameras within the two surgical lights units 202 and 204 can capture a plurality of images of the surgical site at the same time. The plurality of images captures the surgical site from different perspectives because the cameras are at installed at different locations and have different orientations.

At block 304, the system identifies an obstruction to the surgical site in an image of the plurality of images. The obstruction can be an object that a surgeon does not expect to appear in his or her field of view during a surgical procedure. In some examples, the obstruction includes a surgeon's head or a surgeon's body because they are not expected to appear in the surgeon's field of view during a surgery. In some examples, the obstruction does not include surgical tools or a surgeon's hand at the surgical site as they are expected to appear in the surgeon's field of view. The identification of the obstruction can be performed using a number of different techniques described below with reference to blocks 304a-e.

At optional block 304a, the system can detect the obstruction in the image by inputting the image into a trained machine-learning model to determine if the image contains an area representing the obstruction. In some examples, the trained machine-learning model is configured to receive an input image and output an indication of an area in the input image as blocking the surgical site or an indication that such area is not detected. For example, the model can receive an input image and output an indication of the pixels in the input image representing the obstruction.

In some examples, the machine-learning model is trained using a training dataset. The training dataset can include a plurality of labeled training images. The training images may be captured by in-light cameras embedded in surgical lights. For each training image, the area (e.g., pixels) representing an obstruction to the surgical site is labeled. During training, each training image is inputted into the machine-learning model to obtain a predicted obstruction area. The predicted obstruction area is then compared against the labeled actual obstruction area. Based on the comparison, the model can be updated accordingly.

In some examples, the machine-learning model is pre-trained for object detection using training images that are not captured by in-light cameras. The model can be then fine-tuned using training images captured by in-light cameras (e.g., using transfer learning) to detect obstructions that occur in surgical settings, such as a surgeon's head and back. In some examples, the machine-learning model is an object detection algorithm such as Yolo-V4. It should be appreciated by one of ordinary skill in the art that other machine-learning models can be used to detect obstruction areas in images in block 304a, such as an RNN model. Further, it should be appreciated by one of ordinary skill in the art that the machine-learning model can be configured in other manners in block 304a. For example, the machine-learning model can be configured to receive an input image and output a value (e.g., a binary value) indicating whether an obstruction has been detected. The training dataset can include a plurality of labeled training images, each labeled as including an obstruction or not including an obstruction. During training, each training image is inputted into the machine-learning model to obtain a determination. The determination is then compared against the ground-truth label. Based on the comparison, the model can be updated accordingly.

At optional block 304b, the system can detect the obstruction by inputting the image into a trained machine-learning model to determine if the image contains the surgical site. If the image does not contain the surgical site, the system detects the obstruction in the image. In some examples, the trained machine-learning model is configured to receive an input image and output an indication of an area in the input image as the surgical site or an indication that such area is not detected. For example, the model can receive an input image and output an indication of the pixels in the input image representing the surgical site.

In some examples, the machine-learning model is trained using a training dataset. The training dataset can include a plurality of labeled training images. The training images may be captured by in-light cameras embedded in surgical lights. For each training image, the area (e.g., pixels) representing a surgical site is labeled. During training, each training image is inputted into the machine-learning model to obtain a predicted surgical site. The predicted obstruction area is then compared against the labeled actual surgical site. Based on the comparison, the model can be updated accordingly.

In some examples, the machine-learning model is pre-trained for object detection using training images that are not captured by in-light cameras. The model can be then fine-tuned using training images captured by in-light cameras (e.g., using transfer learning) to detect surgical sites. In some examples, the machine-learning model is an object detection algorithm such as Yolo-V4. It should be appreciated by one of ordinary skill in the art that other machine-learning models can be used to detect obstruction areas in images in block 304b, such as an RNN model. Further, it should be appreciated by one of ordinary skill in the art that the machine-learning model can be configured in other manners in block 304b. For example, the machine-learning model can be configured to receive an input image and output a value (e.g., a binary value) indicating whether a surgical site has been detected. The training dataset can include a plurality of labeled training images, each labeled as including a surgical site or not including a surgical site. During training, each training image is inputted into the machine-learning model to obtain a determination. The determination is then compared against the ground-truth label. Based on the comparison, the model can be updated accordingly.

At optional block 304c, the system detects the obstruction by obtaining a proximity measurement of an in-light sensor associated with the in-light camera that captured the image. In some examples, each in-light camera of the plurality of in-light cameras is associated with one or more in-light sensors in the same surgical light unit. Each sensor can be configured to obtain a proximity measurement indicative of the distance between the corresponding camera and what is captured by the corresponding camera. The system then compares the proximity measurement with a predefined threshold. The predefined threshold can be set to a range within which the surgical site is not expected to be present but obstruction (the surgeon's head and back) may be present. Based on the comparison, the system determines whether the image captured by the in-light camera includes the obstruction. For example, if the proximity measure falls within the range, the system can determine that the image captured by the corresponding camera at the same time includes an obstruction to the surgical site.

In some examples, the in-light sensor comprises a capacitive sensor, a Doppler sensor, an inductive sensor, a magnetic sensor, an optical sensor, a LiDAR sensor, a sonar sensor, an ultrasonic sensor, a radar sensor, or a hall effect sensor. It should be appreciated by one of ordinary skill in the art that the in-light sensor can include any sensor capable of obtaining proximity information.

At optional block 304d, the system can detect the obstruction by obtaining pixel-wise depth information of the image. For example, the system can determine, for each pixel in an image, the depth between the camera and the object captured in the image. An obstruction to the surgical site, such as a surgeon's head and back, is closer to the camera than the surgical site. Thus, the system can compare the pixel-wise depth information with a predefined threshold and, based on the comparison, determine whether an image captured by the in-light camera include the obstruction. The predefined threshold can be set to a range within which the surgical site is not expected to be present but obstruction (the surgeon's head and back) may be present. For example, if the pixel-wise depth information is lower than the predefined threshold (e.g., 1 meter), the system can determine that an obstruction to the surgical site is captured in the image.

At optional block 304e, the system can detect the obstruction by obtaining an auto-focus distance of the in-light camera that captured the image. In the auto focus mode, the in-light camera focuses on an object that is filling most of the field of view, and the camera focus motor position can be used to detect the auto-focus distance (i.e., the distance between the camera and the object focused on). Because a surgeon's head and upper body are at lesser distance than the surgical site from the camera, the surgeon's head and upper body would cause the camera to autofocus to a closer distance if they appear in the field of view. Thus, the system can compare the auto-focus distance with a predefined threshold and, based on the comparison, determine whether an image captured by the in-light camera include the obstruction. The predefined threshold can be set to a range within which the surgical site is not expected to be present but obstruction (the surgeon's head and back) may be present. For example, if the auto-focus distance is lower than the predefined threshold (e.g., 1 meter), the system can determine that the image would include an obstruction to the surgical site.

At block 306, responsive to identifying the obstruction, the system generates a composite image based on a set of the plurality of images. The composite image excludes the obstruction. In some examples, the system identifies in the image the area representing the obstruction and replaces pixels in the area with pixels from images in the set of images to eliminate any obstructed zones at the surgical site. For example, the system identifies that the image includes a surgeon's head blocking part of the surgical site, and uses images taken by other in-light cameras at the same time to fill in the obstruction area.

Identification of the obstruction area in the image can be performed using a number of techniques. In some examples, identification of the obstruction area is based on a machine-learning model (e.g., the model described with reference to block 304a). In some examples, identification of the obstruction area is based on pixel-wise depth information as described with reference to block 304d. In some examples, identification of the obstruction area is based on proximity measurements as described with reference to block 304c.

After the obstruction area is identified in the image, the blocked pixels can be digitally replaced using other images captured by other in-light cameras. Because the relative positions of the other in-light cameras are known and the overlapping pixels among the images are known, pixels from the other images that depict the unobstructed surgical site can be selected and used to fill in the image to generate a composite image. In some examples, the composite image is generated using a machine-learning model. The machine-learning model can be configured to receive a plurality of images and generate a composite image in which the obstruction area is eliminated.

In some examples, the composite image can have enhanced properties such as higher resolution, depth of focus, and dynamic range than an image from a single camera. Such an image may eliminate the need for mechanical zoom.

At block 308, the system displays the composite image as the intraoperative image of the surgical site. In some examples, multiple surgical lights are provided to illuminate the same surgical site and multiple displays are provided to display the video streams from the multiple surgical lights. For example, with reference to FIG. 2A, a first display 210 corresponding to the first surgical light unit 202 and a second display 212 corresponding to the second surgical light unit 204 are simultaneously used, and the composite image is included in one of the displays. For example, when a camera in the surgical light 202 captures an obstruction, a composite image can be generated based on images captured from other cameras in the surgical light 202 and/or cameras in the surgical light 204 and displayed in the display 210. Similarly, when a camera in the surgical light 204 captures an obstruction, a composite image can be generated based on images captured from other cameras in the surgical light 204 and/or cameras in the surgical light 202 and displayed in the display 212. During surgical procedures, surgeons can view the displays 210 and 212, which can provide enhanced visibility of the surgical site, and conduct the operation accordingly.

Figure 5:
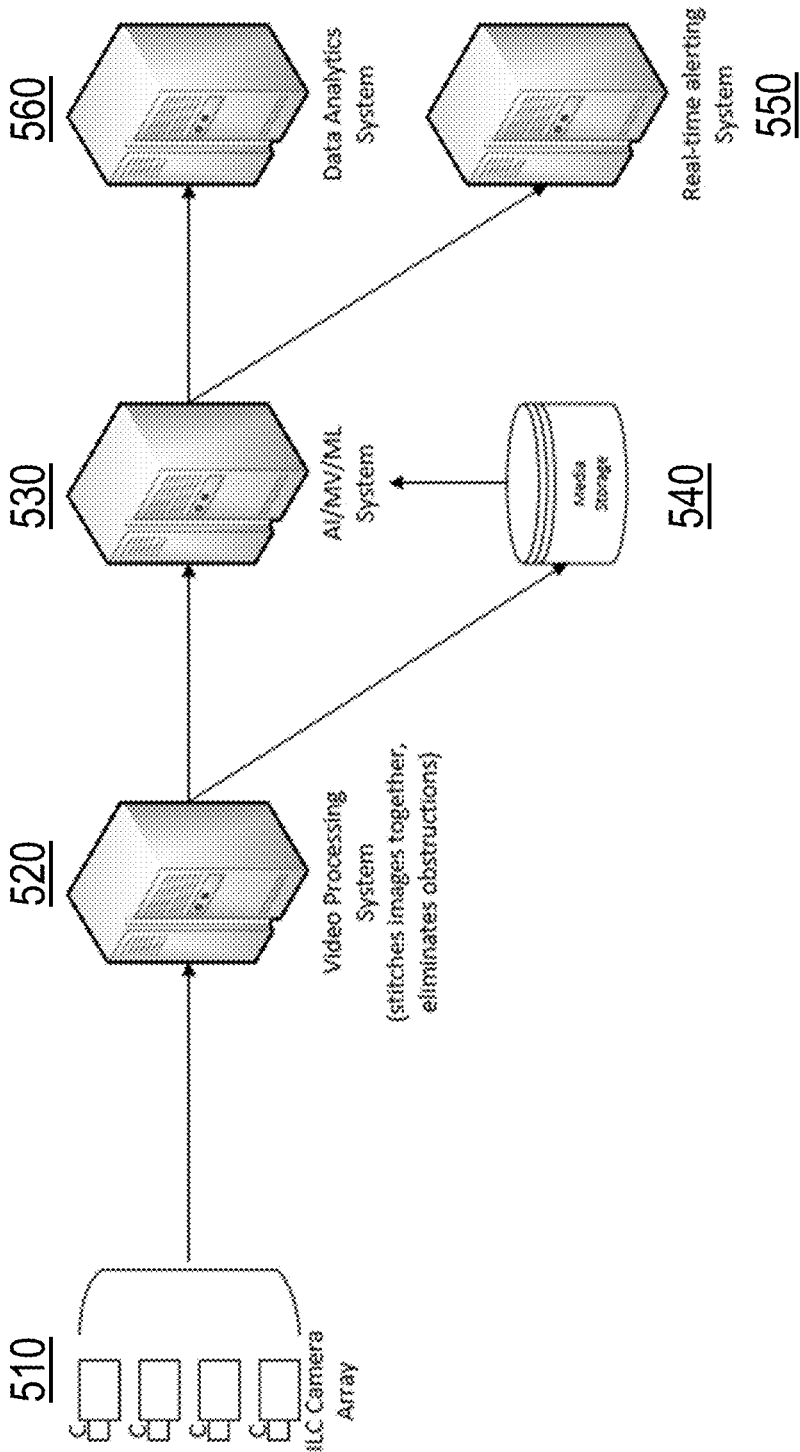
FIG. 5 illustrates an exemplary workflow for obtaining images from in-light cameras and performing downstream analyses, in accordance with some examples.

In some examples, the system further inputs the composite image into a trained machine-learning model to detect an issue and outputs an alert based on the issue. FIG. 5 illustrates an exemplary workflow for obtaining images from in-light cameras and performing downstream analyses. As shown, images captured by multiple in-light cameras 510 can be provided to video processing system 520, which can generate a composite image to eliminate obstructions. The resulting image can be stored at media storage 540 and displayed as a part of a video data transmission stream to observe the operation. The image can further be provided to the AI system 530 and the data analytics system 560. The AI system 530 can identify an issue based on the image, such as one or more of peripheral tissue damage (e.g., accidental or unrecognized damage), incorrect procedures, undiagnosed issues, and retained surgical bodies. In some examples, the AI system comprises one or more models that are configured to receive an input image and identify an issue with the image. Recognition of patient risk issues are fed to the real-time alerting system 550, for example, for surgical staff notification.

Figure 4B:
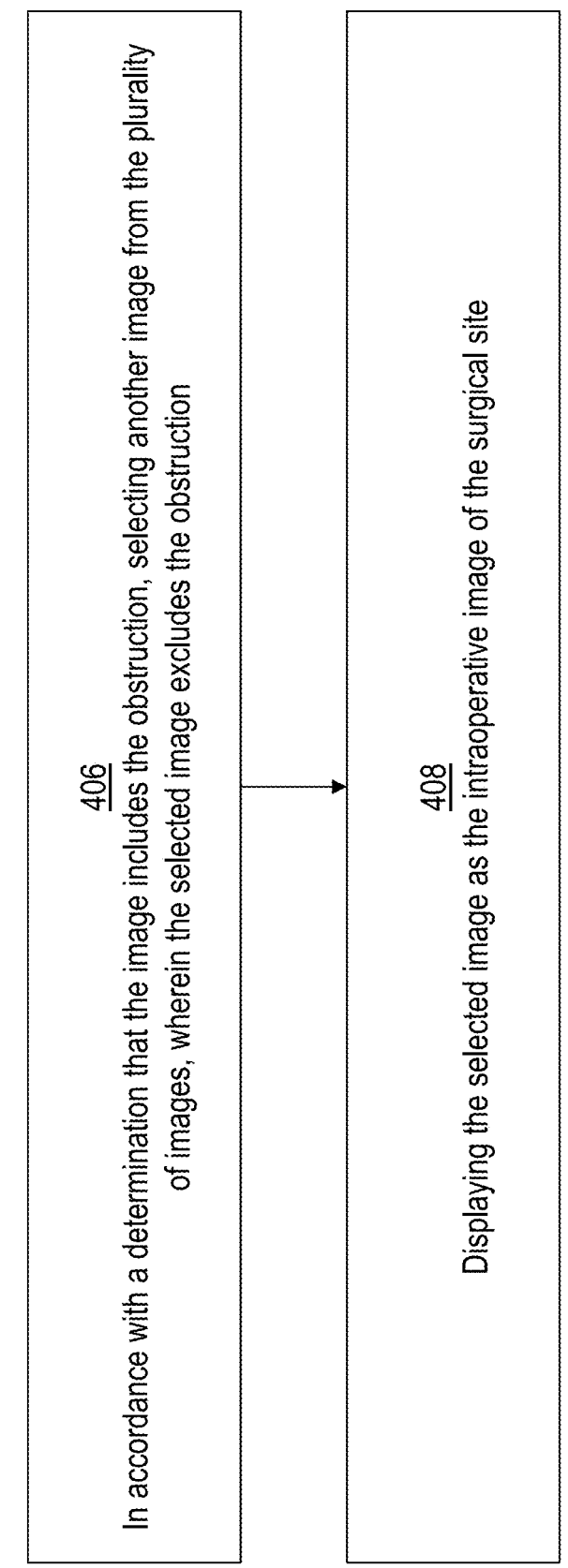

FIGS. 4A and 4B illustrate an exemplary process 400 for displaying an intraoperative image of a surgical site, in accordance with some examples. Process 400 is performed, for example, using one or more electronic devices implementing a software platform. In some examples, process 400 is performed using a client-server system, and the blocks of process 400 are divided up in any manner between the server and one or more client devices. In other examples, process 400 is performed using only a client device or only multiple client devices. In process 400, some blocks are, optionally, combined, the order of some blocks is, optionally, changed, and some blocks are, optionally, omitted. In some examples, additional steps may be performed in combination with the process 400. Accordingly, the operations as illustrated (and described in greater detail below) are exemplary by nature and, as such, should not be viewed as limiting.

At block 402, the system receives a plurality of images captured by a plurality of cameras. The plurality of images capture the surgical site from a plurality of different perspectives. In some examples, the plurality of cameras are in-light cameras integrated into one or more surgical light units illuminating the surgical site. In some examples, the plurality of images is captured at a same time. In some examples, at least one of the plurality of cameras are not integrated into a surgical light unit, such as cameras 252 and 254 in FIG. 2B.

In some examples, the plurality of in-light cameras is integrated into a single surgical light unit. For example, with reference to FIG. 1A, the plurality of in-light cameras can be two or more of the cameras installed in the surgical light 12, such as the central camera 22 and the peripheral cameras surrounding the central camera (e.g., camera 23). During a surgical procedure, the cameras within the surgical light 12 can capture a plurality of images of the surgical site at the same time. The plurality of images captures the surgical site from different perspectives because the cameras are at installed at different locations and have different orientations.

In some examples, the plurality of in-light cameras can be located in different light heads. For example, with reference to FIG. 2A, the plurality of cameras can comprise: a first set of one or more in-light cameras integrated into the first surgical light unit 202 illuminating the surgical site and a second set of one or more in-light cameras integrated into the second surgical light unit 204 illuminating the surgical site. During a surgical procedure, the cameras within the two surgical lights units 202 and 204 can capture a plurality of images of the surgical site at the same time. The plurality of images captures the surgical site from different perspectives because the cameras are at installed at different locations and have different orientations.

At block 404, the system identifies an obstruction to the surgical site in an image of the plurality of images. The obstruction can be an object that a surgeon does not expect to appear in the field of view during a surgical procedure. In some examples, the obstruction includes a surgeon's head or a surgeon's body because they are not expected to appear in the field of view during a surgery. In some examples, the obstruction does not include surgical tools or a surgeon's hand at the surgical site as they are expected to appear in the surgeon's field of view. The identification of the obstruction can be performed using a number of different techniques described below with reference to blocks 404*a-e*.

At optional block 404*a,* the system can detect the obstruction in the image by inputting the image into a trained machine-learning model to determine if the image contains an area representing the obstruction. In some examples, the trained machine-learning model is configured to receive an input image and output an indication of an area in the input image as blocking the surgical site or an indication that such area is not detected. For example, the model can receive an input image and output an indication of the pixels in the input image representing the obstruction.

In some examples, the machine-learning model is trained using a training dataset. The training dataset can include a plurality of labeled training images. The training images may be captured by in-light cameras embedded in surgical lights. For each training image, the area (e.g., pixels) representing an obstruction to the surgical site is labeled. During training, each training image is inputted into the machine-learning model to obtain a predicted obstruction area. The predicted obstruction area is then compared against the labeled actual obstruction area. Based on the comparison, the model can be updated accordingly.

In some examples, the machine-learning model is pre-trained for object detection using training images that are not captured by in-light cameras. The model can be then fine-tuned using training images captured by in-light cameras (e.g., using transfer learning) to detect obstructions that occur in surgical settings, such as a surgeon's head and back. In some examples, the machine-learning model is an objection detection algorithm such as Yolo-V4. It should be appreciated by one of ordinary skill in the art that other machine-learning models can be used to detect obstruction areas in images in block 404*a*, such as an RNN model. Further, it should be appreciated by one of ordinary skill in the art that the machine-learning model can be configured in other manners in block 404*a*. For example, the machine-learning model can be configured to receive an input image and output a value (e.g., a binary value) indicating whether an obstruction has been detected. The training dataset can include a plurality of labeled training images, each labeled as including an obstruction or not including an obstruction. During training, each training image is inputted into the machine-learning model to obtain a determination. The determination is then compared against the ground-truth label. Based on the comparison, the model can be updated accordingly.

At optional block 404*b*, the system can detect the obstruction by inputting the image into a trained machine-learning model to determine if the image contains the surgical site. If the image does not contain the surgical site, the system detects the obstruction in the image.

In some examples, the trained machine-learning model is configured to receive an input image and output an indication of an area in the input image as the surgical site or an indication that such area is not detected. For example, the model can receive an input image and output an indication of the pixels in the input image representing the surgical site. In some examples, the machine-learning model is trained using a training dataset. The training dataset can include a plurality of labeled training images. The training images may be captured by in-light cameras embedded in surgical lights. For each training image, the area (e.g., pixels) representing a surgical site is labeled. During training, each training image is inputted into the machine-learning model to obtain a predicted surgical site. The predicted obstruction area is then compared against the labeled actual surgical site. Based on the comparison, the model can be updated accordingly.

In some examples, the machine-learning model is pre-trained for object detection using training images that are not captured by in-light cameras. The model can be then fine-tuned using training images captured by in-light cameras (e.g., using transfer learning) to detect surgical sites. In some examples, the machine-learning model is an objection detection algorithm such as Yolo-V4. It should be appreciated by one of ordinary skill in the art that other machine-learning models can be used to detect obstruction areas in images in block 404*b*, such as an RNN model. Further, it should be appreciated by one of ordinary skill in the art that the machine-learning model can be configured in other manners in block 404*b*. For example, the machine-learning model can be configured to receive an input image and output a value (e.g., a binary value) indicating whether a surgical site has been detected. The training dataset can include a plurality of labeled training images, each labeled as including a surgical site or not including a surgical site. During training, each training image is inputted into the machine-learning model to obtain a determination. The determination is then compared against the ground-truth label. Based on the comparison, the model can be updated accordingly.

At optional block 404*c,* the system detects the obstruction by obtaining a proximity measurement of an in-light sensor associated with the in-light camera that captured the image.

In some examples, each in-light camera of the plurality of in-light cameras is associated with one or more in-light sensors in the same surgical light unit. Each sensor can be configured to obtain a proximity measurement indicative of the distance between the corresponding camera and what is captured by the corresponding camera. The system then compares the proximity measurement with a predefined threshold. The predefined threshold can be set to a range within which the surgical site is not expected to be present but obstruction (the surgeon's head and back) may be present. Based on the comparison, the system determines whether the image captured by the in-light camera includes the obstruction. For example, if the proximity measure falls within the range, the system can determine that the image captured by the corresponding camera at the same time includes an obstruction to the surgical site.

In some examples, the in-light sensor comprises a capacitive sensor, a Doppler sensor, an inductive sensor, a magnetic sensor, an optical sensor, a LiDAR sensor, a sonar sensor, an ultrasonic sensor, a radar sensor, or a hall effect sensor. It should be appreciated by one of ordinary skill in the art that the in-light sensor can include any sensor capable of obtaining proximity information.

At optional block 404*d,* the system can detect the obstruction by obtaining pixel-wise depth information of the image. For example, the system can determine, for each pixel in an image, the depth between the camera and the object captured in the image. An obstruction to the surgical site, such as a surgeon's head and back, is closer to the camera than the surgical site. Thus, the system can compare the pixel-wise depth information with a predefined threshold and, based on the comparison, determine whether an image captured by the in-light camera include the obstruction. The predefined threshold can be set to a range within which the surgical site is not expected to be present but obstruction (the surgeon's head and back) may be present. For example, if the pixel-wise depth information is lower than the predefined threshold (e.g., 1 meter), the system can determine that an obstruction to the surgical site is captured in the image.

At optional block 404*e,* the system can detect the obstruction by obtaining an auto-focus distance of the in-light camera that captured the image. In the auto focus mode, the in-light camera focuses on an object that is filling most of field of view, and the camera focus motor position can be used to detect the auto-focus distance (i.e., the distance between the camera and the object focused on). Because a surgeon's head and upper body are at lesser distance than the surgical site from the camera, the surgeon's head and upper body would cause the camera to autofocus to a closer distance if they appear in the field of view. Thus, the system can compare the auto-focus distance with a predefined threshold and, based on the comparison, determine whether an image captured by the in-light camera include the obstruction. The predefined threshold can be set to a range within which the surgical site is not expected to be present but obstruction (the surgeon's head and back) may be present. For example, if the auto-focus distance is lower than the predefined threshold (e.g., 1 meter), the system can determine that the image would include an obstruction to the surgical site.

At block 406, responsive to identifying the obstruction, the system selects another image from the plurality of images, wherein the selected image excludes the obstruction or includes less of the obstruction than the image analyzed in block 404. For example, the system can select the least obstructed image out of the plurality of images for display. In some examples, the image is selected by a user or based on preferences of the user.

At block 408, the system displays the selected image as the intraoperative image of the surgical site. In some examples, multiple surgical lights are provided to illuminate the same surgical site and multiple displays are provided to display the video streams from the multiple surgical lights. For example, with reference to FIG. 2A, a first display 210 corresponding to the first surgical light unit 202 and a second display 212 corresponding to the second surgical light unit 204 are simultaneously used, and the selected image is included in one of the displays. For example, when a camera in the surgical light 202 captures obstruction, a different image can be selected from images captured from other cameras in the surgical light 202 and/or cameras in the surgical light 204 and displayed in the display 210. Similarly, when a camera in the surgical light 204 captures obstruction, a different image can be selected from images captured from other cameras in the surgical light 204 and/or cameras in the surgical light 202 and displayed in the display 212. During surgical procedures, surgeons can view the displays 210 and 212, which can provide enhanced visibility of the surgical site, and conduct the surgeries accordingly. Accordingly, in-light cameras can now be used for guiding surgeries, rather than simply for remote observation.

FIG. 6 illustrate an exemplary process 600 for displaying an intraoperative image of a surgical site, in accordance with some examples. Process 600 is performed, for example, using one or more electronic devices implementing a software platform. In some examples, process 600 is performed using a client-server system, and the blocks of process 600 are divided up in any manner between the server and one or more client devices. In other examples, process 600 is performed using only a client device or only multiple client devices. In process 600, some blocks are, optionally, combined, the order of some blocks is, optionally, changed, and some blocks are, optionally, omitted. In some examples, additional steps may be performed in combination with the process 600. Accordingly, the operations as illustrated (and described in greater detail below) are exemplary by nature and, as such, should not be viewed as limiting.

At block 602, the system receives a plurality of images captured by a plurality of cameras. The plurality of images capture the surgical site from a plurality of different perspectives. In some examples, the plurality of images is captured at a same time. In some examples, at least one of the plurality of cameras are not integrated into a surgical light unit, such as cameras 252 and 254 in FIG. 2B. In some examples, the cameras are integrated into one or more surgical light units, as shown in FIGS. 1 and 2A.

At block 604, the system generates, based on the plurality of images, a synthetic image that captures the surgical site from a synthetic perspective different from the plurality of perspectives. The synthetic image is associated with a new angle of view that may have not existed previously.

Figure 7A:
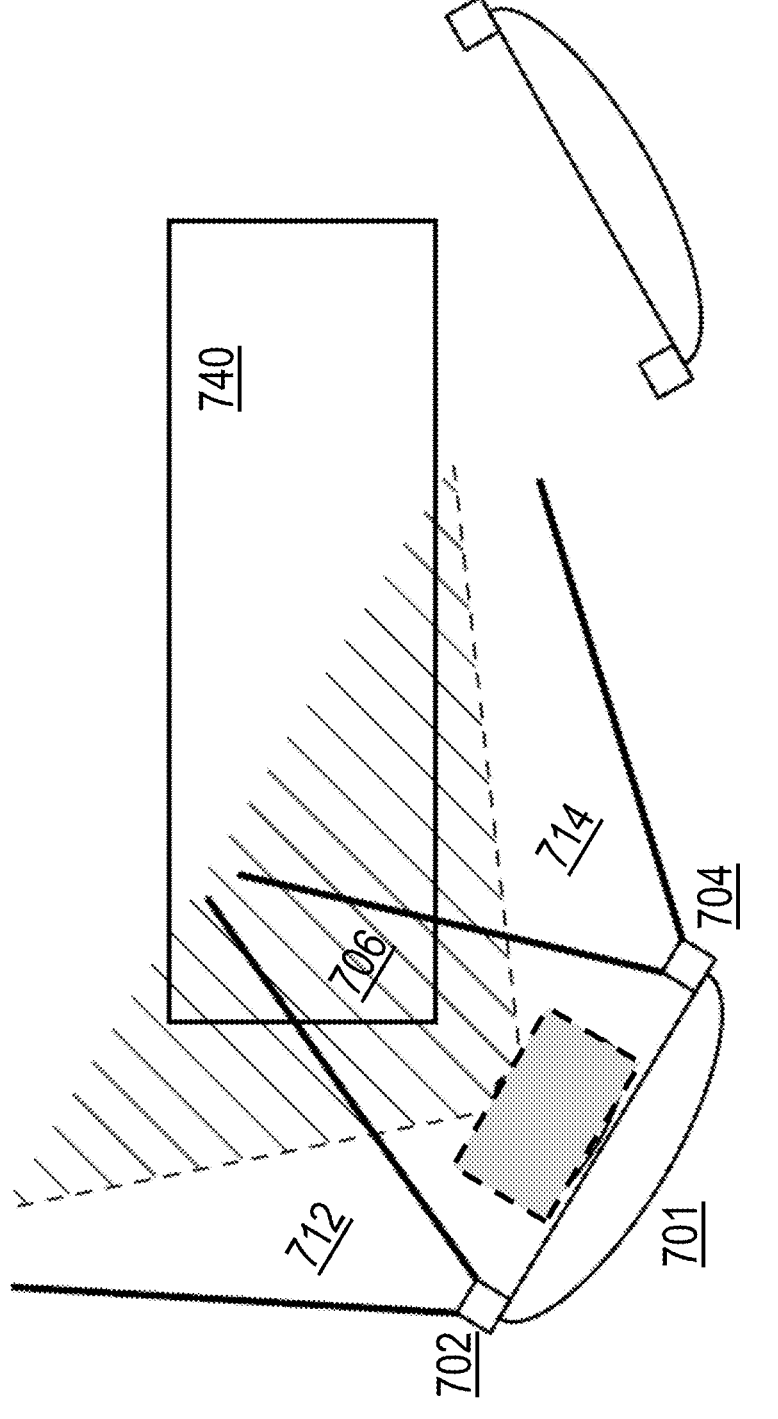
FIG. 7A illustrate an exemplary surgical setup, in accordance with some examples.

In some examples, the plurality of cameras is integrated into a single surgical light unit. FIG. 7A illustrates an exemplary surgical setup, in accordance with some examples. A surgical light unit 701 illuminates a surgical site on the surgical table 740. The surgical light unit comprises two cameras 702 and 704 that capture the surgical site from two different perspectives 712 and 714, respectively. Based on the images captured by cameras 702 and 704, the system can generate a synthetic image having a synthetic perspective 706. In the depicted example, the two cameras 702 and

704 are peripheral cameras within the light unit 701, and the synthetic perspective is from the center of the light unit 701.

In some examples, cameras 702 and 704 have different focal lengths. For example, camera 702 can be a wide angle lens camera and the camera 704 can be a telephoto lens camera. The synthetic image can be a medium focal length image.

Figure 7B:
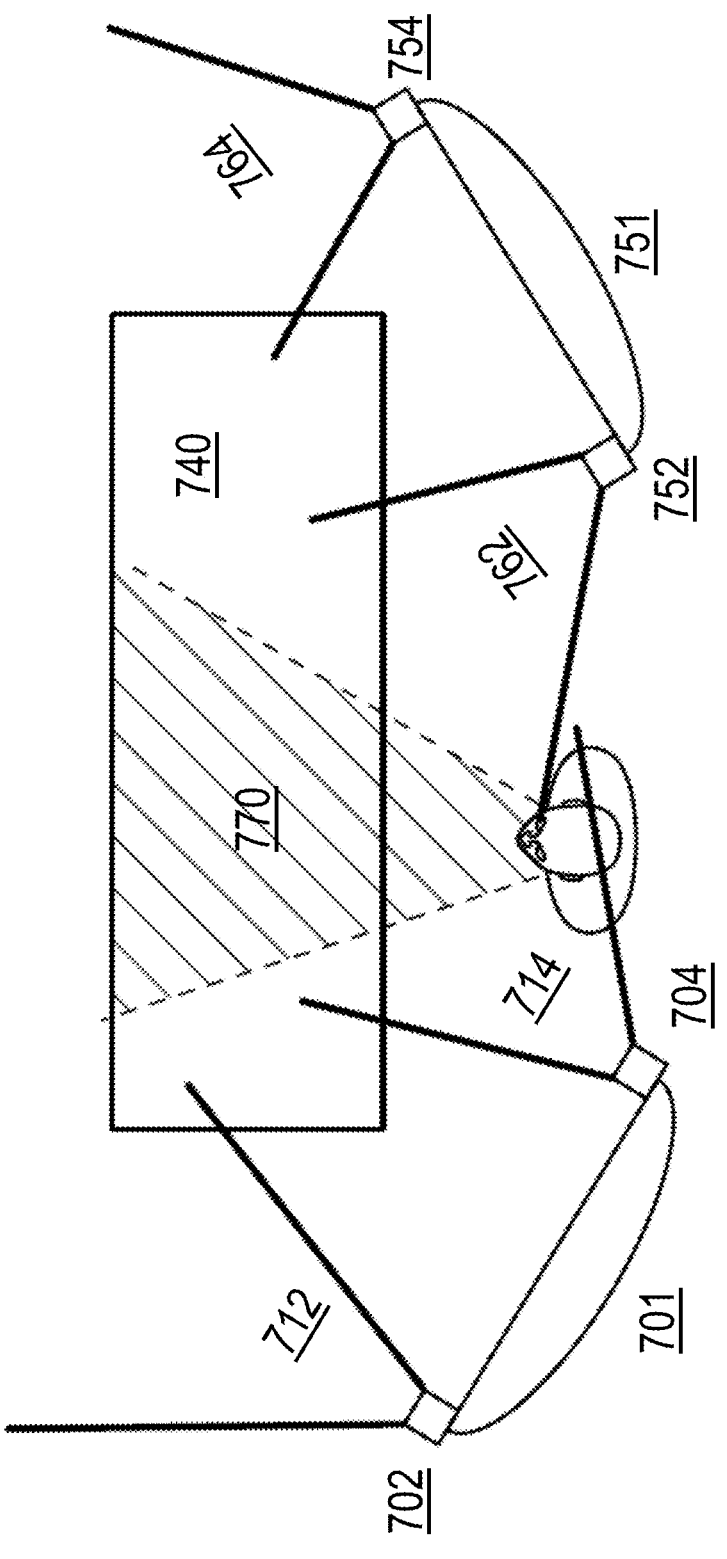
FIG. 7B illustrate an exemplary surgical setup, in accordance with some examples.

In some examples, the plurality of cameras is integrated into multiple surgical light units. FIG. 7B illustrates an exemplary surgical setup, in accordance with some examples. Surgical light unit 701 and 751 illuminate a surgical site on the surgical table 740. Surgical light unit 701 includes cameras 702 and 704 capturing the surgical site from two different perspectives 712 and 714, respectively. Surgical light unit 751 includes cameras 752 and 754 capturing the surgical site from two different perspectives 762 and 764, respectively. Based on the images captured by the cameras, the system can generate a synthetic image that captures the surgical site from a synthetic perspective 770. In the depicted example, the synthetic image is from the perspective that provides a view that humans are accustomed to seeing (e.g., from the perspective of a surgeon that would stand by the surgical table). In some examples, the synthetic image is from a perspective from a location where it would be difficult to physically place a camera. In some examples, the synthetic image can be augmented by various technologies to improve the fidelity and fill in any potential gaps of irregularities.

In some examples, the system can dynamically shift the synthetic perspective to avoid obstructions such as the head or body of the clinical staff or surgeon.

In some examples, the system generates the synthetic image having a synthetic perspective to avoid an obstruction to the surgical site upon detecting such obstruction in an image of the plurality of images. The obstruction can be detected using any of the techniques described herein.

At block 606, the system displays the synthetic image as the intraoperative image of the surgical site. In some examples, multiple surgical lights are provided to illuminate the same surgical site and multiple displays are provided to display the video streams from the multiple surgical lights. For example, with reference to FIG. 2A, a first display 210 corresponding to the first surgical light unit 202 and a second display 212 corresponding to the second surgical light unit 204 are simultaneously used, and the synthetic image is included in one of the displays. During surgical procedures, surgeons can view the displays 210 and 212, which can provide enhanced visibility of the surgical site, and conduct the operation accordingly. In some examples, the system further inputs the synthetic image into a trained machine-learning model to detect an issue and outputs an alert based on the issue, as described with reference to FIG. 5 herein.

In some examples, the techniques described herein can be enabled and disabled based on user inputs. For example, when the surgical light(s) are pointed to the ceiling (e.g., for endoscopic surgeries), the user can configure the surgical light(s) to not detect obstruction.

Although some examples described herein involve processing of image data captured by in-light cameras embedded in one or more surgical lights, it should be appreciated that the techniques described herein can be applied to any image data, including images that are captured by cameras outside surgical lights in the operating room, to provide unobstructed intraoperative images of the surgical site.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The foregoing description, for purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated.

What is claimed is:

1. A method of displaying an intraoperative image of a surgical site, comprising:
    receiving a plurality of images captured by a plurality of in-light cameras integrated into a surgical light unit illuminating the surgical site, the surgical light unit comprising a plurality of sensors, wherein the plurality of images capture the surgical site from a plurality of different perspectives, wherein the plurality of in-light cameras of the surgical light unit comprises a central in-light camera protruding from the surgical light unit and one or more peripheral in-light cameras surrounding the central in-light camera;
    automatically orienting an image captured by the central in-light camera such that a top of the image captured by the central in-light camera is aligned with a top of the surgical light unit based on information from one or more sensors of the plurality of sensors;
    determining a presence of an obstruction to the surgical site in the image captured by the central in-light camera;
    in accordance with a determination that the obstruction is not present, displaying the image captured by the central in-light camera as the intraoperative image of the surgical site; and
    in accordance with a determination that the obstruction is present:
        generating a composite image based on a set of the plurality of images, wherein the composite image excludes the obstruction; and
        displaying the composite image as the intraoperative image of the surgical site.

2. The method of claim 1, wherein the plurality of images is captured at a same time.

3. The method of claim 1, comprising:
    receiving a second plurality of images captured by a second plurality of in-light cameras integrated into a second surgical light unit illuminating the surgical site.

4. The method of claim 3, further comprising:
    simultaneously displaying a first view corresponding to the first surgical light unit and a second view corresponding to the second surgical light unit, wherein the composite image is included in one of the first view and the second view.

5. The method of claim 1, wherein the obstruction includes a surgeon's head or a surgeon's body and does not include surgical tools or a surgeon's hand at the surgical site.

6. The method of claim 1, wherein determining the presence of the obstruction to the surgical site in the image comprises:

inputting the image into a trained machine-learning model to determine if the image contains an area representing the obstruction.

7. The method of claim 6, wherein the trained machine-learning model is configured to receive an input image and detect an area in the input image as blocking the surgical site.

8. The method of claim 6, wherein the machine-learning model is trained using a plurality of labelled training images.

9. The method of claim 6, wherein the machine learning model is trained by pre-training the machine learning model based on a plurality of training images that were not captured by in-light cameras and fine-tuning the machine learning model based on a plurality of training images captured by in-light cameras.

10. The method of claim 1, wherein determining the presence of the obstruction to the surgical site in the image comprises:
    inputting the image into a trained machine-learning model to determine if the image contains the surgical site; and
    if the image does not contain the surgical site, detecting the obstruction in the image.

11. The method of claim 10, wherein the trained machine-learning model is configured to receive an input image and detect an area in the input image as the surgical site.

12. The method of claim 10, wherein the machine-learning model is trained using a plurality of labelled training images.

13. The method of claim 1, wherein each in-light camera of the plurality of in-light cameras is associated with an in-light sensor in the same surgical light unit.

14. The method of claim 13, wherein determining the presence of the obstruction to the surgical site in the image comprises:
    obtaining a proximity measurement of an in-light sensor associated with the in-light camera that captured the image;
    comparing the proximity measurement with a predefined threshold; and
    based on the comparison, determining whether the image includes the obstruction.

15. The method of claim 14, wherein the in-light sensor comprises a capacitive sensor, a Doppler sensor, an inductive sensor, a magnetic sensor, an optical sensor, a LiDAR sensor, a sonar sensor, an ultrasonic sensor, a radar sensor, or a hall effect sensor.

16. The method of claim 1, wherein determining the presence of the obstruction to the surgical site in the image comprises:
    obtaining an auto-focus distance of the in-light camera that captured the image;
    comparing the auto-focus distance with a predefined threshold; and
    based on the comparison, determining whether the image includes the obstruction.

17. The method of claim 1, wherein determining the presence of the obstruction to the surgical site in the image comprises:
    obtaining pixel-wise depth information of the image;
    based on the pixel-wise depth information, determining whether the image includes the obstruction.

18. The method of claim 1, wherein generating the composite image based on the set of the plurality of images comprises: identifying, in an image from the plurality of images, an area representing the obstruction; and replacing pixels in the area with pixels from the set of images.

19. The method of claim 1, wherein at least one in-light camera of the plurality of in-light cameras comprises a fisheye lens.

20. The method of claim 19, further comprising: performing correction to an image captured by the at least one in-light camera to compensate for distortion caused by the fisheye lens.

21. The method of claim 1, further comprising: automatically reorienting one or more of the plurality of in-light cameras.

22. The method of claim 1, further comprising: reorienting one or more of the plurality of in-light cameras based on a user input.

23. The method of claim 1, further comprising:

inputting the composite image into a trained machine-learning model to detect an issue; and outputting an alert based on the issue.

24. The method of claim 23, wherein the issue comprises one or more of peripheral tissue damage, incorrect procedures, undiagnosed issues, and retained surgical bodies.

25. The method of claim 1, wherein the composite image is displayed as part of a video image transmission stream.

26. A system for displaying an intraoperative image of a surgical site, comprising:

a display;

one or more processors;

a memory; and one or more programs, wherein the one or more programs are stored in the memory and configured to be executed by the one or more processors, the one or more programs including instructions for:

receiving a plurality of images captured by a plurality of in-light cameras integrated into a surgical light unit illuminating the surgical site, the surgical light unit comprising a plurality of sensors, wherein the plurality of images capture the surgical site from a plurality of different perspectives, wherein the plurality of in-light cameras of the surgical light unit comprises a central in-light camera protruding from the surgical light unit and one or more peripheral in-light cameras surrounding the central in-light camera;

automatically orienting an image captured by the central in-light camera such that a top of the image captured by the central in-light camera is aligned with a top of the surgical light unit based on information from one or more sensors of the plurality of sensors;

determining a presence of an obstruction to the surgical site in the image captured by the central in-light camera;

in accordance with a determination that the obstruction is not present, displaying the image captured by the central in-light camera as the intraoperative image of the surgical site; and in accordance with a determination that the obstruction is present:

generating a composite image based on a set of the plurality of images, wherein the composite image excludes the obstruction; and displaying the composite image as the intraoperative image of the surgical site.

\* \* \* \* \*